United States Patent [19]

Zondler et al.

[11] Patent Number: 4,851,028
[45] Date of Patent: Jul. 25, 1989

[54] METHOD OF COMBATING UNDESIRABLE PLANT GROWTH AND OF REGULATING PLANT GROWTH

[75] Inventors: Helmut Zondler, Bottmingen, Switzerland; Wolfgang Eckhardt, Lörrach, Fed. Rep. of Germany; Robert Nyfeler, Basel; Hans-Georg Brunner, Lausen, both of Switzerland

[73] Assignee: Ciba-Geigy Corporation, Ardsley, N.Y.

[21] Appl. No.: 92,252

[22] Filed: Sep. 2, 1987

[30] Foreign Application Priority Data

Sep. 5, 1986 [CH] Switzerland .................. 3583/86

[51] Int. Cl.⁴ .......................................... A01N 43/54
[52] U.S. Cl. .......................................... 71/76; 71/90; 71/92; 544/60; 544/122; 544/229; 544/295; 544/322
[58] Field of Search .................. 71/76, 90, 92

[56] References Cited

U.S. PATENT DOCUMENTS

| | | | |
|---|---|---|---|
| 4,315,931 | 2/1982 | Scharwaechter et al. | 544/322 |
| 4,404,213 | 9/1983 | Ten Haken et al. | 546/305 |
| 4,718,934 | 1/1988 | Zondler et al. | 71/76 |
| 4,767,443 | 8/1988 | Zondler et al. | 71/92 |

FOREIGN PATENT DOCUMENTS

| | | |
|---|---|---|
| 0129433 | 12/1984 | European Pat. Off. |
| 0175651 | 3/1986 | European Pat. Off. |
| 1926547 | 1/1970 | Fed. Rep. of Germany |

Primary Examiner—Richard L. Raymond
Assistant Examiner—James H. Turnipseed
Attorney, Agent, or Firm—Kevin T. Mansfield; Edward McC. Roberts

[57] ABSTRACT

A method of combating undesirable plant growth and of regulating plant growth, which comprises allowing a herbicidal or plant-regulating amount of a compound of the formula I

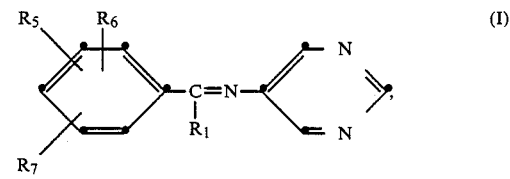

in which $R_1$ is $SR_2$; $OR_2$; $O-CHR_{10}R_2$; $N(R_3)(CHR_{10}R_4)$; $N(R_{11})(CHR_{10}R_4)$ or $NR_3R_4$; $R_2$ is optionally substituted $C_1-C_{10}$-alkyl $C_1-C_4$-haloalkyl; $C_3-C_8$-alkenyl; (3-methyloxetan-3-yl)methyl; $C_3-C_8$-alkynyl; or an optionally substituted radical from the group comprising phenyl, benzyl, $C_3-C_7$-cycloalkyl, furanyl or furfuryl $R_3$ and $R_4$ independently of one another are hydrogen; an optionally substituted phenyl or benzyl radical; $C_1-C_8$-alkyl; or $C_3-C_6$-cycloalkyl; or $R_3$ and $R_4$, together with the nitrogen atom, form a saturaated 5- or 6-membered heterocyclic ring which contains up to two heteroatoms from the group comprising N, O and S and can be mono- or disubstituted by $C_1-C_4$-alkyl; $R_5$ is hydrogen; halogen; $C_1-C_8$-alkyl; $C_1-C_4$-alkoxy, $C_1-C_4$-haloalkyl; nitro; cyano; $C_1-C_4$-haloalkoxy; phenylthio; di-$C_1-C_4$- alkylamino; phenyl; or is optionally substituted phenoxy; and $R_6$ and $R_7$ independently of one another are hydrogen; halogen; $C_1-C_8$-alkyl; $C_1-C_4$-haloalkyl; $C_1-C_4$-alkoxy; $C_1-C_4$-haloalkoxy; nitro; cyano; or di-$C_1-C_4$-alkylamino, and $R_{10}$ and $R_{11}$ independently of one another are $C_1-C_4$-alkyl; and salts of compounds of the formula I with acids and bases, to act on the plants or on the environment of the plants, and novel compounds of the formula I'

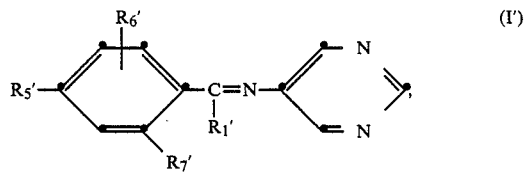

process for their preparation and herbicidal or plant growth-regulating compositions containing these novel compounds.

8 Claims, No Drawings

METHOD OF COMBATING UNDESIRABLE PLANT GROWTH AND OF REGULATING PLANT GROWTH

The invention relates to a method of combating undesirable plant growth and of regulating plant growth.

Fungicidally active 5-arylmethyliminopyrimidines have been disclosed in European Patent Application EP-A 175,651. Surprisingly, it has now been found that 5-arylmethyliminopyrimidines of the general formula I have a herbicidal action against numerous weeds and grasses.

The invention thus relates to a method of combating undesirable plant growth and of regulating plant growth, which comprises allowing a compound of the formula I

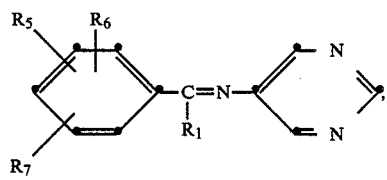

in which $R_1$ is $SR_2$; $OR_2$; $O-CHR_{10}R_2$; $N(R_3)(CHR_{10}R_4)$; $N(R_{11})(CHR_{10}R_4)$ or $NR_3R_4$; $R_2$ is $C_1-C_{10}$-alkyl which is unsubstituted or substituted by hydroxyl, mercapto, $C_1-C_4$-alkoxycarbonyl, mercaptoalkoxy, $C_1-C_4$-alkoxy, $C_1-C_4$-alkylcarbonyl, mono- or di-$C_1-C_4$-alkylamino, $C_1-C_4$-haloalkoxy, tri-$C_1-C_4$-alkoxy)-silyl, cyano, nitro or phenyl; $C_1-C_4$-haloalkyl; $C_3-C_8$-alkenyl; (3-methyloxetan-3-yl)methyl; $C_3-C_8$-alkynyl; or a radical from the group comprising phenyl, benzyl, $C_3-C_7$-cycloalkyl, furanyl or furfuryl which is unsubstituted or mono-, di- or trisubstituted by identical or different substituents from the group comprising halogen, $C_1-C_4$-alkyl, $C_1-C_4$-alkylcarbonyl, nitro, $C_1-C_4$-alkoxy and $C_1-C_4$-haloalkyl; $R_3$ und $R_4$ independently of one another are hydrogen; a phenyl or benzyl radical which is unsubstituted or mono-, di-, tri- or tetrasubstituted by identical or different substituents from the group comprising halogen, $C_1-C_4$-alkyl, $C_1-C_4$-alkylcarbonyl, nitro, $C_1-C_4$-alkoxy, $C_1-C_4$-haloalkyl, $C_1-C_4$-alkylthio and $C_1-C_4$-haloalkylthio; $C_1-C_8$-alkyl; or $C_3-C_6$-cycloalkyl; or $R_3$ and $R_4$, together with the nitrogen atom, form a saturated 5- or 6-membered heterocyclic ring which contains up to two heteroatoms from the group comprising N, O and S and can be mono- or disubstituted by $C_1-C_4$-alkyl; $R_5$ is hydrogen; halogen; $C_1-C_8$-alkyl; $C_1-C_4$-alkoxy; $C_1-C_4$-haloalkyl; nitro; cyano; $C_1-C_4$-haloalkoxy; phenylthio; di-$C_1-C_4$-alkylamino; phenyl; or is phenoxy which is unsubstituted or substituted by the radicals $R_8$ and $R_9$; and $R_6$, $R_7$, $R_8$ and $R_9$ independently of one another are hydrogen; halogen; $C_1-C_8$-alkyl; $C_1-C_4$-haloalkyl; $C_1-C_4$-alkoxy; $C_1-C_4$-haloalkoxy; nitro; cyano; $C_1-C_4$-haloalkoxy; phenylthio; di-$C_1-C_4$-alkylamino; phenyl; or is phenoxy which is unsubstituted or substituted by the radicals $R_8$ and $R_9$; and $R_6$, $R_7$, $R_8$ and $R_9$ independently of one another are hydrogen; halogen; $C_1-C_8$-alkyl; $C_1-C_4$-haloalkyl; $C_1-C_4$-alkoxy; $C_1-C_4$-haloalkoxy; nitro; cyano; or di-$C_1-C_4$-alkylamino; and $R_{10}$ and $R_{11}$ independently of one another are $C_1-C_4$-alkyl; and salts of the compounds of the formula I with acids and bases, to act on the plants or on the environment of the plants.

In the above definition, the generic terms given include, for example, the following specific individual substituents, this list not representing a limitation to the invention:

Alkyl includes straight-chain or branched $C_1-C_{10}$-alkyl, such as methyl, ethyl, n-propyl, isopropyl, n-butyl, sec-butyl, tert-butyl, isobutyl, the isomeric pentyl radicals, for example tert.-pentyl (1,1-dimethylpropyl), and isopentyl (1-ethylpropyl), and the isomeric hexyl, heptyl, octyl, nonyl and decyl radicals. $C_1-C_4$-Alkyl radicals are preferred.

Halogen is fluorine, chlorine, bromine or iodine. Haloalkyl is alkyl according to the particular range defined which is completely or partly substituted by identical or different halogen atoms, for example 2,2,2-trifluoroethyl, 1,1,1,3,3,3-hexafluoroprop-2-yl, trifluoromethyl or difluoromethyl.

$C_3-C_8$-Alkenyl includes both the structurally isomeric and the cis/transisomeric propenyl, butenyl, pentenyl, hexenyl, heptenyl and octenyl radicals. $C_3-C_5$-Alkenyl, for example allyl, is preferred.

$C_3-C_8$-Alkynyl includes the isomeric propynyl, butynyl, pentynyl, hexynyl, heptynyl and octynyl radicals. $C_3-C_5$-Alkynyl, for example propargyl or 2-methylbut-3-yn-2-yl, is preferred.

Alkoxycarbonyl radicals are, inter alia, methoxycarbonyl, ethoxycarbonyl and the isomeric propoxycarbonyl and butoxycarbonyl radicals.

Alkoxy in the context of the particular range defined for the isomeric alkoxy radicals is primarily methoxy or ethoxy.

Alkyl substituted by mercaptoalkoxy radicals is, for example, 2-(2-mercaptoethoxy)-ethyl.

Haloalkoxy and haloalkylthio in the context of the particular range defined are the isomeric alkyl radicals which are mono- or polysubstituted by halogen, for example trifluoromethoxy, 2,2,2-trifluoroethoxy, trifluoromethylthio or 2,2,3,3,3-pentafluoropropoxy.

Alkoxyalkyl radicals are, inter alia: 2-ethoxyethyl, 2-methoxyethyl, 3-methoxypropyl, 2-methoxy-1-methylethyl and methoxymethyl.

$C_3-C_6$-Cycloalkyl is cyclopropyl, cyclobutyl, cyclopentyl and cyclohexyl.

Saturated 5- or 6-membered heterocyclic radicals with up to two heteroatoms from the group comprising N, O and S are: pyrrolidinyl, piperidinyl, piperazinyl, morpholinyl, thiomorpholinyl and thiazolidinyl. The heterocyclic radicals can be mono- or disubstituted by $C_1-C_4$-alkyl, for example the 2,6-dimethylmorpholin-4-yl radical or the 3-ethylpiperidinyl radical.

Tri-$C_1-C_4$-alkoxysilyl is a group which is trisubstituted by identical or different alkoxy radicals, such as triethoxysilyl, diethoxy-tert.-butoxy-silyl or trimethoxy-silyl.

Di-$C_1-C_4$-alkylamino is a group which is substituted by identical or different alkyl radicals, such as dimethylamino, diethylamino or methylethylamino.

In the other substituents, which are composed of several basic elements, the component elements can be freely chosen within the range defined and are as defined above.

The use of compounds of the formula I in which $R_1$ is $SR_2$; $OR_2$; $O-CHR_{10}R_2$; $N(R_3)$ $(CHR_{10}R_4)$; $N(R_{11})$ $(CHR_{10}R_4)$ or $NR_3R_4$; $R_2$ is $C_1-C_6$-alkyl which is unsubstituted or substituted by hydroxyl, mercapto, methoxycarbonyl, phenyl, di-$C_1-C_2$-alkylamino, cyano, nitro, $C_1-C_2$-alkoxy, acetyl or tri-($C_1-C_4$-alkoxy)-silyl; $C_7-C_{10}$-alkyl; (3-methyl-oxetan-3-yl)methyl; $C_1-C_3$- fluoroalkyl; propenyl; $C_3-C_5$-alkynyl; furanyl; furfuryl; or phenyl which is unsubstituted or mono-, di- or trisubstituted by fluorine, chlorine, methyl, methoxy or trifluoromethyl; or $C_5-C_6$-cycloalkyl which is unsubstituted or monosubstituted by chlorine; $R_3$ is hydrogen; or $C_1-C_3$-alkyl; $R_4$ is hydrogen; $C_1-C_5$-alkyl; a phenyl radical which is unsubstituted or mono- or disubstituted by methyl, methoxy, fluorine, chlorine, bromine or nitro; or $C_3-C_6$-cycloalkyl; or $R_3$ and $R_4$, together with the nitrogen atom, are piperazinyl; pyrrolidinyl; or morpholinyl or piperidinyl which is unsubstituted or mono- or disubstituted by methyl or ethyl; $R_5$ is bonded in the para-position relative to the carbimino group and is hydrogen; fluorine; chlorine; bromine; $C_1-C_4$-alkyl; dimethylamino; trifluoromethyl; phenylthio; nitro; iodine; cyano; methoxy; phenyl; or is phenoxy which is unsubstituted or substituted by the radicals $R_8$ and $R_9$; and $R_6$ and $R_7$ independently of one another are hydrogen; chlorine; fluorine; bromine; iodine; methyl; trifluoromethyl; 2,2,2-trifluoroethoxy; nitro; difluoromethyl; or dimethylamino; and $R_8$ and $R_9$ independently of one another are hydrogen; fluorine; chlorine; bromine; methyl; or trifluoromethoxy; and $R_{10}$ and $R_{11}$ independently of one another are $C_1-C_4$-alkyl; and the salts of the compounds of the formula I with acids and bases as herbicides or growth regulators is to be singled out.

The use of compounds of the formula I in which $R_1$ is $OR_2$; $SR_2$; $O-CHR_{10}R_2$; $N(R_3)(CHR_{10}R_4)$; $N(R_{11})(CHR_{10}R_4)$; or $NR_3R_4$; $R_2$ is $C_1-C_6$-alkyl; 2-[tri-(ethoxy)-silyl]ethyl; 2-[tri-(methoxy)-silyl]ethyl, 2-[(diethoxy)-(tert.-butoxy)silyl]ethyl; propenyl; $C_3-C_5$-alkynyl; cyclohexyl; 4-chlorophenyl; p-tolyl; m-tolyl; benzyl; 4-chlorobenzyl; furfuryl; 2-chlorophenyl; 2-bromophenyl; 3-bromophenyl; 3,5-dichlorophenyl; 2,3,5-trichlorophenyl; 4-fluorophenyl; 3,4-dimethylphenyl; 3,5-dimethylphenyl; 2-dimethylamino-2-methylethyl; 2,2,3,3,3-pentafluoropropyl; 2-methoxy-1-methylethyl or 2,2,2-trifluoroethyl; $R_3$ is hydrogen; methyl; or ethyl; $R_4$ is hydrogen; $C_2-C_5$-alkyl; phenyl; cyclopropyl or cyclohexyl; or $R_3$ and $R_4$, together with the nitrogen atom, are 2,6-dimethylmorpholinyl or 3-ethylpiperidinyl; $R_5$ is bonded in the para-position relative to the carbimino group and is hydrogen; fluorine; chlorine; bromine; iodine; methyl; trifluoromethyl; nitro; tert.-butyl; or methoxy; $R_6$ is hydrogen; chlorine; fluorine; 2,2,2-trifluoroethoxy or iodine; and $R_7$ is hydrogen; $R_8$ is hydrogen; or chlorine; and $R_9$ is hydrogen; and $R_{10}$ and $R_{11}$ independently of one another are $C_1-C_4$-alkyl; as herbicides or growth regulators is preferred.

The use of compounds of the formula i in which $R_1$ is $SR_2$; $OR_2$; or $NR_3R_4$; $R_2$ is $C_1-C_6$-alkyl; phenyl; chlorophenyl; or tolyl; $R_3$ is hydrogen; and $R_4$ is $C_1-C_5$-alkyl; and $R_5$ is in the para-position relative to the carbimino group and is hydrogen; fluorine; chlorine; or bromine; and $R_6$ is hydrogen; fluorine; chlorine; or bromine; and $R_7$ is hydrogen; as herbicides or growth regulators is also preferred.

On the basis of the good tolerance towards crop plants, the following groups of compounds of the formula I are to mentioned-observing the definition of each of the other substituents:

Group A

Compounds of the formula I in which $R_1$ is $SR_2$.

Group B

Compounds of the formula I in which $R_1$ is $OR_2$ or $OCHR_{10}R_2$.

Group C

Compounds of the formula I in which $R_1$ is $NR_3R_4$, $N(R_3)$ $(CHR_{10}R_4)$ or $N(R_{11})(CHR_{10}R_4)$.

The following compounds may be mentioned as typical representatives of the substance class according to the invention. They can be prepared by processes analogous to those described in European Patent EP-A 175,651 or have already been made known from this reference in the literature (the melting points, which are uncorrected, are given in [°C.]):

TABLE 1

Compounds of the formula

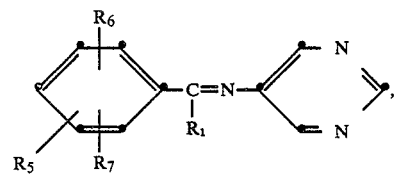

(I)

| Compound No. | $R_5$ | $R_6$ | $R_7$ | $R_1$ | Physical constants |
|---|---|---|---|---|---|
| 1.001 | 4-Cl | 2-Cl | H | $SC(CH_3)_3$ | m.p. 108–109° |
| 1.002 | 4-Cl | 2-Cl | H | $SCH_3$ | m.p. 85–87° |
| 1.003 | 4-Cl | 2-Cl | H | $SCH(CH_3)_2$ | m.p. 76–78° |
| 1.004 | 4-Cl | 2-Cl | H | $SCH_2CH_2CH_3$ | $n_D^{40}$ 1.6123 |
| 1.005 | 4-Cl | 2-Cl | H | $S(CH_2)_9CH_3$ | |
| 1.006 | 4-Cl | 2-Cl | H | $SCH_2CH_2N(C_2H_5)_2$ | |
| 1.007 | 4-Cl | 2-Cl | H | 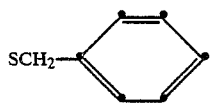 | $n_D^{48}$ 1.6465 |
| 1.008 | 4-Cl | 2-Cl | H | $SCH_2CH\equiv CH_2$ | |

TABLE 1-continued

Compounds of the formula

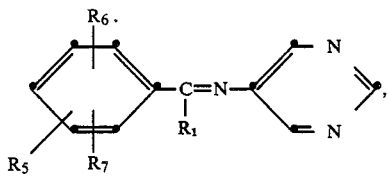

| Compound No. | $R_5$ | $R_6$ | $R_7$ | $R_1$ | Physical constants |
|---|---|---|---|---|---|
| 1.009 | 4-Cl | 2-Cl | H | benzothiophene | m.p. 86–88° |
| 1.010 | 4-Cl | 2-Cl | H | benzothiophene | |
| 1.011 | 4-Cl | 2-Cl | H | $OCH_3$ | $n_D^{24}$ 1.5965 |
| 1.012 | 4-Cl | 2-Cl | H | $OCH(CH_3)_2$ | m.p. 85–86° |
| 1.013 | 4-Cl | 2-Cl | H | $OC(CH_3)_3$ | m.p. 103–104° |
| 1.014 | 4-Cl | 2-Cl | H | $OCH_2CF_3$ | m.p. 96–98° |
| 1.015 | 4-Cl | 2-Cl | H | $OCH_2CH_2CN$ | |
| 1.016 | 4-Cl | 2-Cl | H | $OCH_2CH_2NO_2$ | |
| 1.017 | 4-Cl | H | H | $SC(CH_3)_3$ | m.p. 129–130° |
| 1.018 | 4-Cl | H | H | $SCH(CH_3)_2$ | m.p. 56–57° |
| 1.019 | 4-Cl | H | H | $SCH_3$ | |
| 1.020 | 4-Cl | H | H | $SCH_2CH(CH_3)_2$ | |
| 1.021 | 4-Cl | H | H | $SCH_2CH_2OH$ | |
| 1.022 | 4-F | H | H | $SCH_3$ | |
| 1.023 | 4-F | H | H | $SC(CH_3)_3$ | m.p. 102–103° |
| 1.024 | 4-F | H | H | $SCH(CH_3)_2$ | $n_D^{28}$ 1.5910 |
| 1.025 | H | 3-F | H | $SC(CH_3)_3$ | m.p. 76° |
| 1.026 | H | 3-F | H | $SC_2H_5$ | $n_D^{25}$ 1.6075 |
| 1.027 | H | 2-F | H | $SCH(CH_3)_2$ | m.p. 48–49° |
| 1.028 | H | 2-Cl | H | $SCH(CH_3)_2$ | m.p. 88–89° |
| 1.029 | 4-Br | 2-Cl | H | $SC(CH_3)_3$ | m.p. 120–121° |
| 1.030 | 4-Br | H | H | $SCH(C_2H_5)(C_3H_7)$ | $n_D^{26}$ 1.6065 |
| 1.031 | H | 5-Br | 2-Br | $SC(CH_3)_3$ | |
| 1.032 | H | 5-Cl | 2-Cl | $SC(CH_3)_3$ | |
| 1.033 | H | 6-Cl | 2-Cl | $SCH_3$ | |
| 1.034 | H | 6-F | 2-F | $SC_2H_5$ | |
| 1.035 | H | 6-F | 2-Cl | $SC(CH_3)_3$ | |
| 1.036 | H | H | 2-J | $SC_3H_7$ | |
| 1.037 | H | H | 3-J | $SC_2H_5$ | |
| 1.038 | 2-J | 3-J | 5-J | $SC_3H_7(n)$ | |
| 1.039 | 4-J | 3-J | 5-J | $SC_3H_7(n)$ | |
| 1.040 | H | 3-J | H | $SC_4H_9(n)$ | |
| 1.041 | 4-Cl | 2-Cl | H | $OCH_2C{\equiv}CH$ | m.p. 133–134° |
| 1.042 | 4-Cl | 2-CH_3 | H | O-phenyl-NO_2 | |
| 1.043 | 4-CH_3 | H | H | $OCH(CH_3)_2$ | $n_D^{24}$ 1.5618 |
| 1.044 | 4-CH_3 | H | H | $SC_2H_5$ | $n_D^{24}$ 1.6183 |
| 1.045 | 4-CH_3 | H | H | benzothiophene | $n_D^{23}$ 1.6080 |
| 1.046 | 4-CH_3 | 2-CH_3 | H | $N(CH_3)_2$ | |
| 1.047 | 4-CH_3 | 3-CH_3 | H | $OCH_2CH_2OCH_3$ | |
| 1.048 | 4-CF_3 | H | H | $SC_3H_7(n)$ | |

TABLE 1-continued

Compounds of the formula

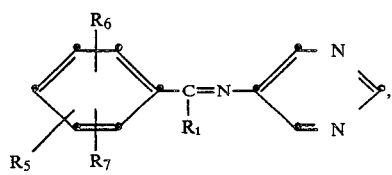
(I)

| Compound No. | R<sub>5</sub> | R<sub>6</sub> | R<sub>7</sub> | R<sub>1</sub> | Physical constants |
|---|---|---|---|---|---|
| 1.049 | H | 3-CF$_3$ | H | (S—⟨phenyl⟩—OCH$_3$) | |
| 1.050 | H | 2-CF$_3$ | H | OCH$_3$ | |
| 1.051 | 4-CH$_3$ | 2-CH$_3$ | 6-CH$_3$ | SC$_3$H$_7$(n) | |
| 1.052 | H | 3-CH$_3$ | H | OC$_2$H$_5$ | |
| 1.053 | 2-CH$_3$ | 3-NO$_2$ | 5-NO$_2$ | OCH$_3$ | |
| 1.054 | 4-NO$_2$ | 3-CH$_3$ | H | SCH(CH$_3$)$_2$ | |
| 1.055 | H | 2-NO$_2$ | 5-CH$_3$ | SCH$_3$ | |
| 1.056 | H | 2-CH$_3$ | H | OCH(CH$_3$)$_2$ | |
| 1.057 | H | 3-CH$_3$ | 2-CH$_3$ | (S—⟨pyridyl, H⟩—Cl) | |
| 1.058 | H | 5-CH$_3$ | 2-CH$_3$ | SCH$_2$CH$_2$N(CH$_3$)$_2$ | |
| 1.059 | H | 5-CH$_3$ | 3-CH$_3$ | (S—⟨phenyl⟩—OCH$_3$) | |
| 1.060 | 4-C(CH$_3$)$_3$ | H | H | SCH(CH$_3$)$_2$ | m.p. 93–94° |
| 1.061 | 4-C(CH$_3$)$_3$ | H | H | OCH$_2$CH(CH$_3$)$_2$ | |
| 1.062 | 4-Cl | 3-NO$_2$ | 5-NO$_2$ | OCH$_3$ | |
| 1.063 | 4-CN | H | H | (CH$_3$O—⟨ring⟩—S—) | |
| 1.064 | 4-NO$_2$ | 2-NO$_2$ | H | N(C$_3$H$_7$)$_2$ | |
| 1.065 | 4-NO$_2$ | 2-NO$_2$ | H | OC$_3$H$_7$(n) | |
| 1.066 | 4-NO$_2$ | 2-NO$_2$ | H | SCH$_2$CH$_2$OH | |
| 1.067 | 4-NO$_2$ | 3-NO$_2$ | H | (SCH$_2$—⟨furyl⟩—O) | |
| 1.068 | H | 5-NO$_2$ | 3-NO$_2$ | O(CH$_2$)$_9$CH$_3$ | |
| 1.069 | 4-NO$_2$ | H | H | SC(CH$_3$)$_3$ | |
| 1.070 | 4-NO$_2$ | H | H | SC$_4$H$_9$(n) | $n_D^{23}$ 1.6138 |
| 1.071 | H | 2-NO$_2$ | H | SCH(CH$_3$)(C$_2$H$_5$) | |
| 1.072 | H | 2-NO$_2$ | H | OCH$_3$ | |
| 1.073 | H | 3-NO$_2$ | H | SCH(CH$_3$)$_2$ | |
| 1.074 | H | 3-NO$_2$ | H | N(CH$_3$)$_2$ | |

TABLE 1-continued

Compounds of the formula

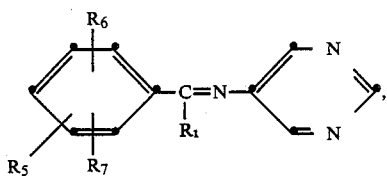

| Compound No. | $R_5$ | $R_6$ | $R_7$ | $R_1$ | Physical constants |
|---|---|---|---|---|---|
| 1.075 | 4-N(CH$_3$)$_2$ | H | H | O—C$_6$H$_5$ | |
| 1.076 | 4-N(CH$_3$)$_2$ | H | H | S—C$_6$H$_4$—F | |
| 1.077 | H | 3-N(CH$_3$)$_2$ | H | SCH$_3$ | |
| 1.078 | H | 5-OCH$_3$ | 3-OCH$_3$ | SCH(CH$_3$)$_2$ | |
| 1.079 | 4-OCH$_3$ | 3-OCH$_3$ | H | SCH(C$_2$H$_5$)(C$_3$H$_7$) | |
| 1.080 | 4-OCH$_3$ | 2-OCH$_3$ | H | OC$_5$H$_{11}$(n) | |
| 1.081 | H | 6-OCH$_3$ | 2-OCH$_3$ | S—C$_6$H$_5$ | |
| 1.082 | H | 3-OCH$_3$ | 2-OCH$_3$ | SCH$_3$ | |
| 1.083 | H | 2-OCH$_3$ | H | SC(CH$_3$)$_3$ | |
| 1.084 | H | 3-OCH$_3$ | H | SCH(CH$_3$)$_2$ | |
| 1.085 | 4-OCH$_3$ | H | H | SCH(CH$_3$)$_2$ | $n_D^{26}$ 1.6084 |
| 1.086 | 4-C$_6$H$_5$ | H | H | SC(CH$_3$)$_3$ | |
| 1.087 | H | 2-C$_6$H$_5$ | H | SC(CH$_3$)$_3$ | |
| 1.088 | 4-Cl | 2-Cl | H | OCH$_2$CH=CH$_2$ | $n_D^{40}$ 1.5830 |
| 1.089 | 4-Cl | 2-Cl | H | SCH$_2$CH(CH$_3$)$_2$ | resin |
| 1.090 | 4-Cl | H | H | S—C$_6$H$_4$CH$_3$(4) | m.p. 155–156° |
| 1.091 | 4-OCH$_3$ | H | H | SC(CH$_3$)$_3$ | m.p. 56–59° |
| 1.092 | 4-Cl | 2-Cl | H | SCH(C$_2$H$_5$)C$_3$H$_7$(n) | $n_D^{48}$ 1.5810 |
| 1.093 | 4-Cl | 2-Cl | H | —N—C$_6$H$_{10}$(C$_2$H$_5$) | $n_D^{48}$ 1.579 |
| 1.094 | 4-Cl | 2-Cl | H | O—C$_6$H$_4$CH$_3$(3) | m.p. 127–128° |
| 1.095 | 4-Cl | 2-Cl | H | N(C$_2$H$_5$)$_2$ | $n_D^{48}$ 1.5900 |
| 1.096 | 4-F | H | H | OCH$_2$CF$_3$ | m.p. 96–97° |
| 1.097 | 4-F | H | H | O—Cyclohexyl | $n_D^{23}$ 1.5638 |
| 1.098 | 4-F | H | H | OCH$_2$CH$_2$CH$_3$ | m.p. 60–61° |
| 1.099 | 4-Cl | 2-Cl | H | OCH$_2$CH$_2$CH$_3$ | m.p. 59–61° |
| 1.100 | 4-Cl | 2-Cl | H | SC$_2$H$_5$ | $n_D^{26}$ 1.6284 |
| 1.101 | 4-Cl | 2-Cl | H | S(CH$_2$)$_3$CH$_3$ | $n_D^{24}$ 1.6087 |
| 1.102 | 4-Cl | 2-Cl | H | SCH$_2$CH$_2$N(CH$_3$)$_2$ | |
| 1.103 | 4-Cl | 2-Cl | H | SCH(CH$_3$)C$_2$H$_5$ | $n_D^{27}$ 1.6075 |
| 1.104 | 4-Cl | 2-Cl | H | SCH$_2$CH$_2$—C$_6$H$_5$ | |
| 1.105 | 4-Cl | 2-Cl | H | SCH$_2$-furyl | |

TABLE 1-continued

Compounds of the formula

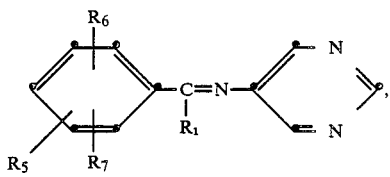
(I)

| Compound No. | R$_5$ | R$_6$ | R$_7$ | R$_1$ | Physical constants |
|---|---|---|---|---|---|
| 1.106 | 4-Cl | 2-Cl | H | OCH$_2$–O (furan-like ring) | m.p. 84–85° |
| 1.107 | 4-Cl | 2-Cl | H | O—Cyclohexyl | m.p. 97–98° |
| 1.108 | 4-Cl | 2-Cl | H | NHC$_4$H$_9$(n) | n$_D^{40}$ 1.5810 |
| 1.109 | 4-Cl | 2-Cl | H | NHCH(CH$_3$)$_2$ | m.p. 115–117° |
| 1.110 | 4-Cl | 2-Cl | H | NHC(CH$_3$)$_3$ | m.p. 153° |
| 1.111 | 4-Cl | 2-Cl | H | NH—Cyclopropyl | m.p. 150–151° |
| 1.112 | 4-Cl | 2-Cl | H | NH—Cyclohexyl | m.p. 194–195° |
| 1.113 | 4-CH$_3$ | H | H | OC(CH$_3$)$_3$ | |
| 1.114 | 4-CH$_3$ | H | H | SC(CH$_3$)$_3$ | m.p. 101–102° |
| 1.115 | 4-C(CH$_3$)$_3$ | H | H | SC(CH$_3$)$_3$ | Smp. 161–162° |
| 1.116 | 4-C(CH$_3$)$_3$ | H | H | OCH(CH$_3$)$_2$ | |
| 1.117 | 4-C(CH$_3$)$_3$ | H | H | SCH(C$_2$H$_5$)C$_3$H$_7$(n) | n$_D^{25}$ 1.5674 |
| 1.118 | 4-C(CH$_3$)$_3$ | H | H | OC(CH$_3$)$_3$ | |
| 1.119 | 4-C(CH$_3$)$_3$ | H | H | NHCH(CH$_3$)$_2$ | |
| 1.120 | H | 2-CF$_3$ | H | SC(CH$_3$)$_3$ | m.p. 81–83° |
| 1.121 | 4-OCH$_3$ | 3-OCH$_3$ | 5-OCH$_3$ | OC(CH$_3$)$_3$ | |
| 1.122 | " | " | " | SC$_2$H$_5$ | |
| 1.123 | " | " | " | SC(CH$_3$)$_3$ | m.p. 123–124° |
| 1.124 | " | " | " | SCH(C$_2$H$_5$)C$_3$H$_7$(n) | m.p. 70° |
| 1.125 | H | 3-N(CH$_3$)$_2$ | H | SC(CH$_3$)$_3$ | |
| 1.126 | H | 3-N(CH$_3$)$_2$ | H | OCH(CH$_3$)C$_2$H$_5$ | |
| 1.127 | H | 2-J | H | SC(CH$_3$)$_3$ | m.p. 126–127 |
| 1.128 | 4-Br | H | H | OCH(CH$_3$)$_2$ | m.p. 95–96° |
| 1.129 | H | 2-J | H | SC$_3$H$_7$(iso) | n$_D^{27}$ 1.6390 |
| 1.130 | H | 2-J | H | SC$_4$H$_9$(iso) | n$_D^{27}$ 1.6240 |
| 1.131 | 4-CN | H | H | SC$_4$H$_9$(tert.) | |
| 1.132 | H | 5-Cl | 3-Cl | SC$_3$H$_7$(iso) | |
| 1.133 | H | 5-Cl | 3-Cl | OC$_4$H$_9$(tert.) | |
| 1.134 | H | 5-Cl | 3-Cl | SC$_4$H$_9$(tert.) | |
| 1.135 | H | 5-Cl | 3-Cl | S—Cyclohexyl | |
| 1.136 | H | 5-Cl | 3-Cl | OCH$_2$CF$_3$ | |
| 1.137 | 4-F | H | H | SCH(C$_2$H$_5$)C$_3$H$_7$(n) | n$_D^{28}$ 1.5710 |
| 1.138 | 4-Cl | H | H | SC$_2$H$_5$ | |
| 1.139 | 4-Cl | H | H | SCH(C$_2$H$_5$)C$_3$H$_7$(n) | |
| 1.140 | 4-Cl | H | H | S—Cyclohexyl | |
| 1.141 | 4-Cl | H | H | OC$_4$H$_9$(tert.) | n$_D^{28}$ 1.5630 |
| 1.142 | 4-Cl | 2-Cl | H | SC(CH$_3$)$_2$C$_2$H$_5$ | m.p. 89° |
| 1.143 | 4-CH$_3$ | H | H | SCH(CH$_3$)$_2$ | m.p. 48–50° |
| 1.144 | 4-Cl | 2-Cl | H | SCH$_2$CH$_2$CH(CH$_3$)$_2$ | n$_D^{24}$ 1,6005 |
| 1.145 | 4-Cl | 2-Cl | H | SCH$_2$CHOH<br>\|<br>CH$_3$ | |
| 1.146 | 4-Cl | 2-Cl | H | SCH$_2$CH$_2$OC$_2$H$_5$ | |
| 1.147 | 4-Cl | 2-Cl | H | SCH$_2$CH$_2$CN | |
| 1.148 | 4-Cl | 2-Cl | H | S—Cyclopentyl | |
| 1.149 | 4-Cl | 2-Cl | H | SCH$_2$COOCH$_3$ | m.p. 76–79° |
| 1.150 | 4-Cl | 2-Cl | H | SCH$_2$CH$_2$Si(OC$_2$H$_5$)$_3$ | n$_D^{24}$ 1.5540 |
| 1.151 | 4-Cl | 2-Cl | H | SCH$_2$CH$_2$CH$_2$Si(OCH$_3$)$_3$ | |
| 1.152 | 4-Cl | 2-F | H | SC(CH$_3$)$_3$ | m.p. 101–103° |
| 1.153 | 4-Cl | 2-F | H | SCH(CH$_3$)$_2$ | m.p. 62–65° |
| 1.154 | 4-Cl | 2-F | H | SC$_3$H$_7$(n) | |
| 1.155 | 4-Cl | 2-F | H | SC$_4$H$_9$(n) | |
| 1.156 | 4-Cl | 2-F | H | S—Benzyl | m.p. 86–89° |
| 1.157 | 4-Cl | 2-F | H | S—C$_6$H$_4$Cl(4) | n$_D^{40}$ 1.6386 |
| 1.158 | 4-Cl | 2-F | H | O—C$_6$H$_4$Cl(4) | m.p. 111–123° |
| 1.159 | 4-Cl | 2-F | H | NHC$_4$H$_9$(sec) | wax |
| 1.160 | 4-Cl | 2-F | H | OC$_3$H$_7$(n) | |
| 1.161 | 4-Cl | 2-F | H | OC$_3$H$_7$(iso) | m.p. 71–75° |
| 1.162 | 4-Cl | 2-F | H | SCH(C$_2$H$_5$)C$_3$H$_7$(n) | |
| 1.163 | 4-Cl | 2-F | H | OC$_4$H$_9$(tert.) | m.p. 65–69° |
| 1.164 | 4-Cl | 2-Cl | H | N(CH$_3$)$_2$ | |
| 1.165 | 4-Cl | H | H | N(CH$_3$)$_2$ | |

TABLE 1-continued

Compounds of the formula (I)

[Structure: benzene ring with R5, R6, R7 substituents, connected via C(R1)=N to a pyrimidine ring]

| Compound No. | R$_5$ | R$_6$ | R$_7$ | R$_1$ | Physical constants |
|---|---|---|---|---|---|
| 1.166 | 4-Cl | H | H | [4-membered N-H ring] | |
| 1.167 | 4-Cl | H | H | [6-membered N-H ring] | |
| 1.168 | 4-Cl | H | H | [ring with N, H, NH] | |
| 1.169 | 4-Cl | H | H | [ring with N, O] | |
| 1.170 | H | H | H | [6-membered N-H ring] | |
| 1.171 | 4-Cl | H | H | [ring with N, S] | |
| 1.172 | H | H | H | [ring with N, O] | |
| 1.173 | 4-Cl | H | H | [ring with N, S] | |
| 1.174 | 4-Cl | 2-Cl | H | OCH(CF$_3$)$_2$ | m.p. 73–74° |
| 1.175 | 4-C$_6$H$_5$ | H | H | SCH$_3$ | |
| 1.176 | " | H | H | SC$_2$H$_5$ | |
| 1.177 | " | H | H | SC$_3$H$_7$(n) | |
| 1.178 | " | H | H | SC$_3$H$_7$(iso) | |
| 1.179 | " | H | H | SC$_4$H$_9$(n) | |
| 1.180 | " | H | H | SC$_4$H$_9$(iso) | |
| 1.181 | " | H | H | SC$_4$H$_9$(sec) | |
| 1.182 | " | H | H | OCH$_3$ | |
| 1.183 | " | H | H | OC$_2$H$_5$ | |
| 1.184 | " | H | H | OC$_3$H$_7$(n) | |
| 1.185 | " | H | H | OC$_3$H$_7$(iso) | |
| 1.186 | " | H | H | OC$_4$H$_9$(n) | |
| 1.187 | " | H | H | OC$_4$H$_9$(iso) | |
| 1.188 | " | H | H | OC$_4$H$_9$(sec) | |
| 1.189 | " | H | H | OC$_4$H$_9$(tert.) | |
| 1.190 | " | H | H | OCH$_2$CH=CH$_2$ | |
| 1.191 | " | H | H | OCH$_2$C≡CH | |

TABLE 1-continued

Compounds of the formula

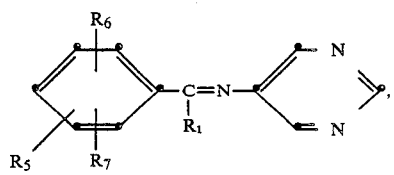 (I)

| Compound No. | $R_5$ | $R_6$ | $R_7$ | $R_1$ | Physical constants |
|---|---|---|---|---|---|
| 1.192 | " | H | H | NHCH$_3$ | |
| 1.193 | " | H | H | NHC$_3$H$_7$(iso) | |
| 1.194 | " | H | H | N(C$_2$H$_5$)$_2$ | |
| 1.195 | " | H | H | (morpholino ring N—O) | |
| 1.196 | H | 2-Cl | H | SC(CH$_3$)$_3$ | m.p. 129–130° |
| 1.197 | H | 2-Cl | H | SC(CH$_3$)$_2$C$_2$H$_5$ | |
| 1.198 | H | 2-Cl | H | NHC(CH$_3$)$_3$ | m.p. 137–138° |
| 1.199 | H | 2-Cl | H | OCH(CH$_3$)$_2$ | m.p. 68–69° |
| 1.200 | H | 2-Cl | H | OC(CH$_3$)$_3$ | m.p. 95–97° |
| 1.201 | H | 2-Cl | H | NHCH(CH$_3$)$_2$ | m.p. 181–182° |
| 1.202 | H | 2-Cl | H | OC$_3$H$_7$(n) | |
| 1.203 | 4-CH$_3$ | 2-CH$_3$ | H | SCH(CH$_3$)$_2$ | m.p. 113° |
| 1.204 | 4-CH$_3$ | 2-CH$_3$ | H | SC(CH$_3$)$_2$C$_2$H$_5$ | |
| 1.205 | 4-CH$_3$ | 2-CH$_3$ | H | OCH(CH$_3$)$_2$ | $n_D^{25}$ 1.554 |
| 1.206 | 4-CH$_3$ | 2-CH$_3$ | H | NHCH(CH$_3$)$_2$ | m.p. 128–129° |
| 1.207 | H | 5-Cl | 2-Cl | OCH(CH$_3$)C$_2$H$_5$ | |
| 1.208 | H | 5-Cl | 2-Cl | OCH(CH$_3$)$_2$ | |
| 1.209 | H | 5-Cl | 2-Cl | OC(CH$_3$)$_3$ | |
| 1.210 | H | 5-Cl | 2-Cl | SCH(CH$_3$)$_2$ | |
| 1.211 | H | 3-Cl | 2-Cl | OC$_2$H$_5$ | |
| 1.212 | H | 3-Cl | 2-Cl | OCH(CH$_3$)$_2$ | |
| 1.213 | H | 3-Cl | 2-Cl | NHCH(CH$_3$)$_2$ | |
| 1.214 | H | 3-Cl | 2-Cl | NHC(CH$_3$)$_3$ | |
| 1.215 | H | 3-Cl | 2-Cl | SC(CH$_3$)$_3$ | |
| 1.216 | H | 3-Cl | 2-Cl | SC(CH$_3$)$_2$C$_2$H$_5$ | |
| 1.217 | H | 3-Cl | 2-Cl | SCH(CH$_3$)C$_2$H$_5$ | |
| 1.218 | 4-Cl | 2-F | H | SCH$_2$CH=CH$_2$ | $n_D^{40}$ 1.6107 |
| 1.219 | 4-Br | 2-Cl | H | SC(CH$_3$)$_3$ | m.p. 106–110° |
| 1.220 | 4-Br | 2-Cl | H | SCH(CH$_3$)$_2$ | m.p. 79–85° |
| 1.221 | 4-Br | 2-Cl | H | SCH$_2$CH=CH$_2$ | |
| 1.222 | 4-Br | 2-Cl | H | SCH$_2$—C$_6$H$_5$ | $n_D^{50}$ 1.6508 |
| 1.223 | 4-Br | 2-Cl | H | S—C$_6$H$_4$(Cl)(4) | |
| 1.224 | 4-Br | 2-Cl | H | O—C$_6$H$_4$(Cl)(4) | $n_D^{50}$ 1.6218 |
| 1.225 | 4-Br | 2-Cl | H | NHCH(CH$_3$)C$_2$H$_5$ | |
| 1.226 | 4-Br | 2-Cl | H | OC(CH$_3$)$_3$ | m.p. 107–111° |
| 1.227 | 4-Cl | 2-Cl | H | O—C$_4$H$_9$(sec) | $n_D^{22.5}$ 1.5655 |
| 1.228 | 4-Cl | 2-Cl | H | NH—C$_4$H$_9$(sec) | m.p. 131–133° |
| 1.229 | 4-Cl | 2-Cl | H | OCH(CH$_3$)C$_3$H$_7$(n) | $n_D^{50}$ 1.5480 |
| 1.230 | 4-Cl | 2-Cl | H | —OCH(CH$_3$)C$_3$H$_7$(i) | $n_D^{50}$ 1.5495 |
| 1.231 | 4-Cl | 2-Cl | H | —NHCH$_2$C(CH$_3$)$_3$ | m.p. 161–162° |
| 1.232 | 4-Cl | 2-Cl | H | —NHCH$_2$CH$_2$CH(CH$_3$)$_2$ | m.p. 120–121° |
| 1.233 | 4-Cl | 2-Cl | H | —NHC(CH$_3$)$_2$C$_2$H$_5$ | m.p. 136–137° |
| 1.234 | 4-Cl | 2-Cl | H | —NHC$_2$H$_5$ | m.p. 143–144° |
| 1.235 | 4-Cl | 2-Cl | H | —NHCH$_3$ | m.p. 137–138° |
| 1.236 | 4-Cl | H | H | —NH—C(CH$_3$)$_3$ | m.p. 137–138° |
| 1.237 | 4-Cl | 2-Cl | H | —NH$_2$ | m.p. 161–162° |
| 1.238 | 4-Cl | H | H | —OC$_3$H$_7$(i) | m.p. 91–92° |
| 1.239 | 4-Cl | H | H | —NHC$_3$H$_7$(i) | m.p. 165–167° |

TABLE 1-continued

Compounds of the formula

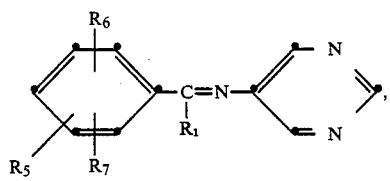

(I)

| Compound No. | R5 | R6 | R7 | R1 | Physical constants |
|---|---|---|---|---|---|
| 1.240 | 4-Cl | 2-Cl | H | —SCH₂CH₂Si(C₄H₉(t))(OC₂H₅)₂ | b.p. 160°/0.05 mm Hg |
| 1.241 | 4-Cl | 2-Cl | H | —N(azetidine) | m.p. 134–135° |
| 1.242 | 4-Cl | 2-Cl | H | —NH—CH(CH₃)(C₃H₇(i)) | m.p. 146–147° |
| 1.243 | 4-Cl | 2-Cl | H | —NH-cyclobutyl | m.p. 147–148° |
| 1.244 | 4-Cl | 2-Cl | H | —OC₂H₅ | m.p. 75–76° |
| 1.245 | 4-Cl | 2-Cl | H | —O—C(CH₃)₂C≡CH | m.p. 138–139° |
| 1.246 | 4-CF₃ | H | H | —OC₃H₇(i) | m.p. 72–75° |
| 1.247 | 4-CF₃ | H | H | —O-(4-Cl-phenyl) | m.p. 81–83° |
| 1.248 | 4-Cl | 2-Cl | H | —O-phenyl | $n_D^{31}$ 1.6100 |
| 1.249 | 4-Cl | H | H | —SC₃H₇(i) | m.p. 56–57° |
| 1.250 | 4-Cl | H | H | —SC(CH₃)₂C₂H₅ | m.p. 71–73° |
| 1.251 | 4-CF₃ | H | H | —S—CH(C₂H₅)(C₃H₇(i)) | Oil |
| 1.252 | 4-Cl | 2-F | H | —O-phenyl | |
| 1.253 | 4-Cl | 2-F | H | —O-(2-CF₃-phenyl) | |
| 1.254 | 4-Cl | 2-Cl | H | —O-(4-Cl-phenyl) | m.p. 94–95° |

TABLE 1-continued
Compounds of the formula
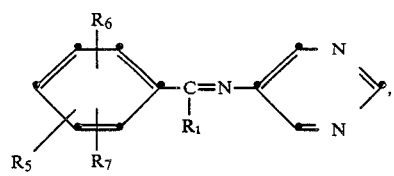
(I)
| Compound No. | R5 | R6 | R7 | R1 | Physical constants |
|---|---|---|---|---|---|
| 1.255 | 4-Cl | 2-Cl | H | ![2-chlorophenoxy] | |
| 1.256 | 4-Cl | 2-Cl | H | ![4-chlorophenoxy] | n_D^25 1,6145 |
| 1.257 | H | 2-F | H | O—CH(CH₃)₂ | m.p. 63–65° |
| 1.258 | H | 2-F | H | NHC(CH₃)₃ | m.p. 127–128° |
| 1.259 | H | 2-F | H | ![phenoxy] | |
| 1.260 | H | 2-F | H | ![4-chlorophenoxy] | m.p. 102–103° |
| 1.261 | H | 2-F | H | ![pyridylthio] | |
| 1.262 | H | 2-F | H | S—C(CH₃)₃ | m.p. 108–109° |
| 1.263 | 4-Cl | 2-F | H | ![pyridylthio] | |
| 1.264 | H | 2-Cl | H | ![phenoxy] | |
| 1.265 | H | 2-Cl | H | ![4-chlorophenoxy] | |
| 1.266 | H | 2-F | H | ![pyridylthio] | |

TABLE 1-continued

Compounds of the formula (I)

| Compound No. | $R_5$ | $R_6$ | $R_7$ | $R_1$ | Physical constants |
|---|---|---|---|---|---|
| 1.267 | H | 2-Cl | H | S—(phenyl) | |
| 1.268 | 4-Cl | H | H | NHC(CH$_3$)$_3$ | m.p. 137–138° |
| 1.269 | 4-Cl | 2-Cl | H | OCH$_2$CF$_2$CF$_3$ | $n_D^{31}$ 1.5151 |
| 1.270 | 4-Cl | 2-Cl | H | OCH(CH$_3$)CH$_2$OCH$_3$ | $n_D^{52}$ 1.5550 |
| 1.271 | 4-Cl | 2-Cl | H | N(CH$_3$)CH(CH$_3$)$_2$ | m.p. 104–106° |
| 1.272 | 4-Cl | 2-Cl | H | SCH$_2$CH$_2$OCH$_2$CH$_2$SH | $n_D^{30}$ 1.6229 |
| 1.273 | 4-Cl | 2-Cl | H | S—(phenyl)—Cl | m.p. 98–99° |
| 1.274 | 4-Cl | 2-Cl | H | S—(phenyl)—CH$_3$ | m.p. 93–94° |
| 1.275 | 4-Cl | 2-Cl | H | NHCH(CH$_3$)CH$_2$OCH$_3$ | m.p. 125–127° |
| 1.276 | 4-Cl | 2-Cl | H | N(CH$_3$)C(CH$_3$)$_3$ | m.p. 106–107° |
| 1.277 | 4-Cl | 2-Cl | H | NHC$_6$H$_5$ | m.p. 163–164° |
| 1.278 | H | 2-Cl | H | OCH$_2$CF$_3$ | |
| 1.279 | H | 2-Cl | H | O—(phenyl)—Br | |
| 1.280 | H | 2-Cl | H | O—(phenyl)—F | m.p. 90–91° |
| 1.281 | 4-CH$_3$ | 2-CH$_3$ | H | SC(CH$_3$)$_3$ | m.p. 120–121° |
| 1.282 | 4-CH$_3$ | 2-CH$_3$ | H | NHC(CH$_3$)$_3$ | m.p. 133–135° |
| 1.283 | 4-CH$_3$ | 2-CH$_3$ | H | OC(CH$_3$)$_3$ | m.p. 60–62° |
| 1.284 | 4-CH$_3$ | 2-CH$_3$ | H | OCH$_2$CF$_3$ | |
| 1.285 | 4-CH$_3$ | 2-CH$_3$ | H | O—(phenyl)—Cl | |

TABLE 1-continued

Compounds of the formula (I)

[Structure: R5, R6, R7-substituted phenyl-C(R1)=N-pyrimidine with two N]

| Compound No. | R5 | R6 | R7 | R1 | Physical constants |
|---|---|---|---|---|---|
| 1.286 | 4-Cl | 2-Cl | H | OCH2COCH3 | |
| 1.287 | 4-Cl | 2-Cl | H | O-C6H4-Br (4-Br) | m.p. 90–92° |
| 1.288 | 4-Cl | 2-Cl | H | O-C6H4-F (4-F) | m.p. 134–135° |
| 1.289 | 4-Cl | 2-Cl | H | O-C6H4-NO2 (4-NO2) | m.p. 140–141° |
| 1.290 | 4-Cl | 2-Cl | H | O-C6H4-OCH3 (4-OCH3) | m.p. 92–94° |
| 1.291 | 4-Cl | 2-Cl | H | O-C6H4-CH3 (4-CH3) | m.p. 94–95° |
| 1.292 | 4-Cl | 2-Cl | H | O-C6H3(Cl)(Cl) (3,4-diCl) | $n_D^{50}$ 1.615 |
| 1.293 | 4-Cl | 2-Cl | H | O-C6H4-COCH3 (4-COCH3) | m.p. 81–82° |
| 1.294 | 4-Cl | 2-Cl | H | O-C6H4-CN (4-CN) | m.p. 167–168° |
| 1.295 | 4-Cl | 2-Cl | H | O-C6H4-Cl (2-Cl) | $n_D^{50}$ 1.612 |
| 1.296 | 4-Cl | 2-Cl | H | NH-C6H4-Cl (2-Cl) | m.p. 98–99° |

TABLE 1-continued
Compounds of the formula
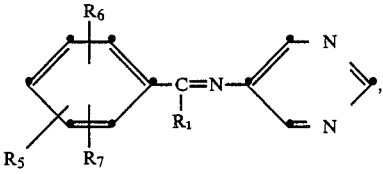 (I)
| Compound No. | R₅ | R₆ | R₇ | R₁ | Physical constants |
|---|---|---|---|---|---|
| 1.297 | 4-Cl | 2-Cl | H | NH—C₆H₄—Cl | |
| 1.298 | 4-Cl | 2-Cl | H | NH—C₆H₄—Br | |
| 1.299 | 4-Cl | 2-Cl | H | NH—C₆H₄—F | |
| 1.300 | 4-Cl | 2-Cl | H | NH—C₆H₄—OCH₃ | m.p. 193—196° |
| 1.301 | 4-Cl | 2-Cl | H | NH—C₆H₄—NO₂ | |
| 1.302 | 4-Cl | 2-Cl | H | NH—C₆H₄—CH₃ | |
| 1.303 | 4-Cl | 2-Cl | H | NH—C₆H₃(Cl)—Cl | m.p. 160–162° |
| 1.304 | 4-Cl | 2-Cl | H | OCH₂—C(CH₃)—O (oxetane) | m.p. 110–112° |
| 1.305 | 4-Cl | 2-Cl | H | OCH(CH₃)—C₆H₅ | m.p. 89–90° |
| 1.306 | 4-Cl | 2-Cl | H | OCH(CH(CH₃)₂)(C₆H₅) | $n_D^{50}$ 1.5769 |
| 1.307 | 4-Cl | 2-Cl | H | OCH(C(CH₃)₃)(C₆H₅) | m.p. 113–114° |

TABLE 1-continued
Compounds of the formula
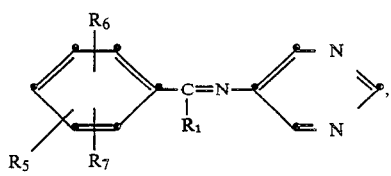
| Compound No. | $R_5$ | $R_6$ | $R_7$ | $R_1$ | Physical constants |
|---|---|---|---|---|---|
| 1.308 | 4-Cl | 2-Cl | H | 2-methoxy-3-chloro-6-methylphenyl (OCH(CH₃)-, Cl) | |
| 1.309 | 4-Cl | 2-Cl | H | OCH(CH₃)-, 4-F phenyl | |
| 1.310 | 4-Cl | 2-Cl | H | OCH(CH₃)-, 3-Br phenyl | |
| 1.311 | 4-Cl | 2-Cl | H | OCH(CH₃)-, 3-NO₂ phenyl | |
| 1.312 | 4-Cl | 2-Cl | H | OCH(C₂H₅)-, 4-CH₃ phenyl | |
| 1.313 | 4-Cl | 2-Cl | H | OCH(C₃H₇)-, 4-F phenyl | |
| 1.314 | 4-Cl | 2-Cl | H | OCH(C₄H₉-n)-, 3-CH₃O phenyl | |

TABLE 1-continued

Compounds of the formula (I)

[Structure: substituted phenyl with R5, R6, R7 substituents connected via C(R1)=N to a pyrimidine ring]

| Compound No. | R$_5$ | R$_6$ | R$_7$ | R$_1$ | Physical constants |
|---|---|---|---|---|---|
| 1.315 | 4-Cl | 2-Cl | H | OCH(C(CH$_3$)$_3$)-(phenyl-Br) | |
| 1.316 | 4-Cl | 2-Cl | H | NHCH(CH$_3$)(C$_6$H$_5$) | m.p. 117–119° |
| 1.317 | 4-Cl | 2-Cl | H | NHCH(CH(CH$_3$)$_2$)(C$_6$H$_5$) | |
| 1.318 | 4-Cl | 2-Cl | H | NHCH(C$_3$H$_7$(n))-(2-Cl-phenyl) | |
| 1.319 | 4-Cl | 2-Cl | H | NHCH(CH$_3$)-(3-OCH$_3$-phenyl) | |
| 1.320 | 4-Cl | 2-Cl | H | NHCH(C$_2$H$_5$)-(4-NO$_2$-phenyl) | |
| 1.321 | 4-Cl | 2-Cl | H | N(C$_4$H$_9$(n))—CH(CH$_3$)(C$_6$H$_5$) | |
| 1.322 | 4-Cl | 2-F | H | OCH$_2$CF$_3$ | m.p. 66–68° |
| 1.323 | 4-Cl | 2-OCH$_2$CF$_3$ | H | OCH$_2$CF$_3$ | n$_D^{50}$ 1.4931 |
| 1.324 | H | 2-F | H | OC$_4$H$_9$(t) | m.p. 73–75° |
| 1.325 | 4-Cl | H | H | NHCH(CH$_3$)$_2$ | m.p. 66–68° |
| 1.326 | 4-Cl | 2-Cl | H | NH—CH(CH$_3$)(C$_6$H$_5$) | m.p. 122–124° (+ Isomer) [α]$_D$ + 63, 8° ± 2°(C$_2$H$_5$OH) |
| 1.327 | 4-Cl | 2-Cl | H | NH—CH(CH$_3$)(C$_6$H$_5$) | m.p. 122–124° (− Isomer) [α]$_D$ − 63, 6° ± 2°(C$_2$H$_5$OH) |

TABLE 1-continued

Compounds of the formula

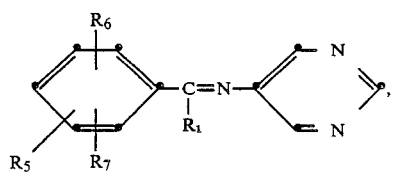

(I)

| Compound No. | R5 | R6 | R7 | R1 | Physical constants |
|---|---|---|---|---|---|
| 1.328 | 4-Cl | 2-Cl | H | OCH$_2$CBr$_3$ | m.p. 134–135° |
| 1.329 | 4-Cl | 2-Cl | H | (morpholine with 2,6-diCH$_3$) | m.p. 153–155° |
| 1.330 | 4-Cl | 2-Cl | H | (morpholine with 2,6-diCH$_3$, N-CH$_3$) | m.p. 157–159° |
| 1.331 | 4-Cl | 2-Cl | H | NHCH(CH$_3$)CH$_2$CH(CH$_3$)$_2$ | n$_D^{50}$ 1.5490 |
| 1.332 | 4-Cl | 2-Cl | H | OCH(CH$_3$)CH$_2$N(CH$_3$)$_2$ | n$_D^{50}$ 1.5673 |
| 1.333 | 4-Cl | 2-Cl | H | SCH$_2$—C$_6$H$_4$—Cl | m.p. 89–90° |
| 1.334 | H | 2-Br | H | OCH(CH$_3$)$_2$ | n$_D^{25}$ 1.5775 |
| 1.335 | H | 2-Br | H | OC(CH$_3$)$_3$ | m.p. 79–81° |
| 1.336 | H | 2-Br | H | SCH(CH$_3$)$_2$ | m.p. 84–85° |
| 1.337 | H | 2-Br | H | SC(CH$_3$)$_3$ | m.p. 119–120° |
| 1.338 | H | 2-Br | H | NHCH(CH$_3$)$_2$ | m.p. 179–181° |
| 1.339 | H | 2-Br | H | NHC(CH$_3$)$_3$ | m.p. 139–141° |
| 1.340 | H | 2-Br | H | O—C$_6$H$_4$—Cl | m.p. 117–119° |
| 1.341 | H | 2-Br | H | O—C$_6$H$_4$—Br | m.p. 116–177° |
| 1.342 | H | 2-CH$_3$ | H | SC(CH$_3$)$_3$ | m.p. 125–127° |
| 1.343 | H | 2-CH$_3$ | H | OCH(CH$_3$)$_2$ | n$_D^{25}$ 1.5565 |
| 1.344 | H | 2-CH$_3$ | H | NHC(CH$_3$)$_3$ | |
| 1.345 | H | 2-CH$_3$ | H | SCH(CH$_3$)$_2$ | m.p. 85–86° |
| 1.346 | H | 2-CH$_3$ | H | OC(CH$_3$)$_2$ | m.p. 92–93° |
| 1.347 | H | 2-CH$_3$ | H | NHCH(CH$_3$)$_2$ | m.p. 137–138° |
| 1.348 | H | 2-CH$_3$ | H | O—C$_6$H$_4$—Cl | m.p. 97–98° |

TABLE 1-continued

Compounds of the formula (I)

[Structure: phenyl ring with R5, R6, R7 substituents, connected via C(R1)=N to a pyrazine/diazine ring]

| Compound No. | R5 | R6 | R7 | R1 | Physical constants |
|---|---|---|---|---|---|
| 1.349 | 4-Cl | H | H | O—(4-Cl-phenyl) | |
| 1.350 | 4-Cl | H | H | O—(2,5-diCl-phenyl) | |
| 1.351 | 4-Cl | H | H | O—(2,4-diCl-phenyl) | |
| 1.352 | 4-Cl | H | H | O—(2,6-diCH3-phenyl) | |
| 1.353 | 2-Cl | 4-Cl | H | O—(2,6-diCl-phenyl) | |
| 1.354 | 2-Cl | 4-Cl | H | O—(2,4-diCl-phenyl) | m.p. 143–145° |
| 1.355 | 2-Cl | 4-Cl | H | O—(2,3,4-triCl-phenyl) | |
| 1.356 | 2-Cl | 4-Cl | H | O—(2,3,5-triCl-phenyl) | m.p. 180–182° |

TABLE 1-continued
Compounds of the formula
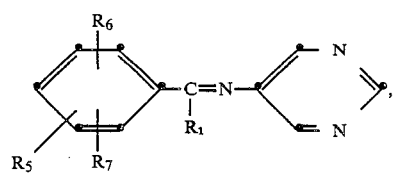
(I)
| Compound No. | R$_5$ | R$_6$ | R$_7$ | R$_1$ | Physical constants |
|---|---|---|---|---|---|
| 1.357 | 2-Cl | 4-Cl | H | 2,4,5-trichlorophenoxy | m.p. 144–145° |
| 1.358 | 2-Cl | 4-Cl | H | 2-bromophenoxy | n$_D^{50}$ 1.6160 |
| 1.359 | 2-Cl | 4-Cl | H | 3-bromophenoxy | m.p. 117–118° |
| 1.360 | 2-Cl | 4-Cl | H | 2-methylphenoxy | m.p. 68–69° |
| 1.361 | 2-Cl | 4-Cl | H | 3-methylphenoxy | m.p. 126–127° |
| 1.362 | 2-Cl | 4-Cl | H | 2,4-dimethylphenoxy | |
| 1.363 | 2-Cl | 4-Cl | H | 2,5-dimethylphenoxy | |
| 1.364 | 2-Cl | 4-Cl | H | 3,4-dimethylphenoxy | m.p. 114–116° |

TABLE 1-continued

Compounds of the formula

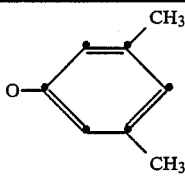

(I)

| Compound No. | $R_5$ | $R_6$ | $R_7$ | $R_1$ | Physical constants |
|---|---|---|---|---|---|
| 1.365 | 2-Cl | 4-Cl | H |  | m.p. 101–102° |
| 1.366 | 2-Cl | 4-Cl | H | 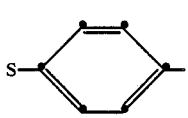 | m.p. 103–104° |
| 1.367 | H | 2-Cl | H | 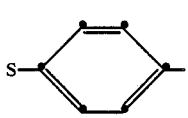 | m.p. 141–142° |
| 1.368 | H | 2-Br | H | OCH(CH$_3$)C$_2$H$_5$ | $n_D^{24}$ 1.570 |
| 1.369 | H | 2-Br | H | SCH(CH$_3$)C$_2$H$_5$ | $n_D^{24}$ 1.610 |
| 1.370 | H | 2-Br | H | 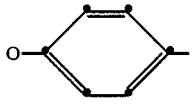 | m.p. 91–92° |
| 1.371 | H | 2-Br | H | 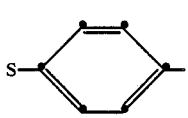 | m.p. 148–149° |

TABLE 2

Compounds of the formula

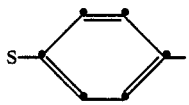

(I)

| Compound No. | $R_6$ | $R_7$ | $R_8$ | $R_9$ | $R_1$ | Physical constants |
|---|---|---|---|---|---|---|
| 2.001 | H | H | H | H | SC(CH$_3$)$_3$ | m.p. 94–96° |
| 2.002 | H | H | H | H | SCH$_3$ | |
| 2.003 | 2-Cl | H | H | H | OCH(CH$_3$)$_2$ | |
| 2.004 | 2-Cl | H | H | H | SC(CH$_3$)$_3$ | |
| 2.005 | 2-CH$_3$ | H | H | H | OCH$_2$CF$_3$ | |
| 2.006 | 2-CH$_3$ | H | H | H | OCH$_3$ | |
| 2.007 | H | H | 4-Cl | H | SC(CH$_3$)$_3$ | m.p. 111–114° |
| 2.008 | H | H | 4-Cl | H | SCH(CH$_3$)$_2$ | Oil |
| 2.009 | H | H | 4-CH$_3$ | H | SCH$_2$CH$_2$CH$_3$ | |
| 2.010 | H | H | 4-CH$_3$ | H | OCH$_2$CF$_3$ | |
| 2.011 | 2-Cl | H | 4-Cl | H | OCH(CH$_3$)$_2$ | m.p. 95° |
| 2.012 | 2-Cl | H | 4-Cl | H | SC(CH$_3$)$_2$ | m.p. 135–136° |
| 2.013 | 2-CH$_3$ | H | 4-CH$_3$ | H | SCH(CH$_3$)$_2$ | |
| 2.014 | 2-CH$_3$ | H | 4-CH$_3$ | H | SCH$_3$ | |
| 2.015 | 2-Cl | H | 4-CH$_3$ | H | SC(CH$_3$)$_3$ | |
| 2.016 | 2-CH$_3$ | H | 4-Cl | H | OCH(CH$_3$)$_2$ | |

TABLE 2-continued

Compounds of the formula

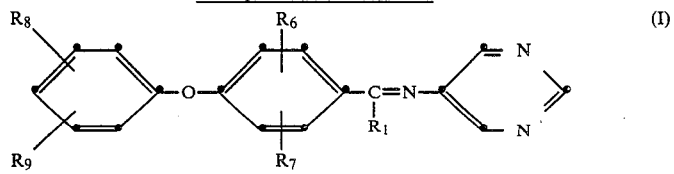
(I)

| Compound No. | R6 | R7 | R8 | R9 | R1 | Physical constants |
|---|---|---|---|---|---|---|
| 2.017 | 2-CH3 | H | 4-Cl | H | OCH3 | |
| 2.018 | 2-CH3 | H | 4-Cl | H | SCH2CH=CH2 | |
| 2.019 | 2-Cl | 3-Cl | 4-Cl | 2-Cl | S—Phenyl | |
| 2.020 | 2-Cl | 3-Cl | 4-CH3 | H | OCH2C≡CH | |
| 2.021 | 2-CH3 | H | 4-Cl | 2-Cl | S—C6H4F(4) | |
| 2.022 | H | H | H | 4-CF3 | SC(CH3)3 | |
| 2.023 | H | H | H | 4-OCF3 | SCH(CH3)2 | |
| 2.024 | H | H | H | H | SCH(CH3)2 | Oil |
| 2.025 | 2-Cl | H | 4-Cl | H | SCH(CH3)2 | m.p. 119–120° |
| 2.026 | 2-Cl | H | 4-Cl | H | OC(CH3)3 | |
| 2.027 | 2-Cl | H | 4-Cl | H | NHCH(CH3)2 | |
| 2.028 | 2-CH3 | H | 4-CH3 | H | SC(CH3)3 | |
| 2.029 | 2-Cl | H | 4-CH3 | H | SC(CH3)3 | |
| 2.030 | 2-Cl | H | 4-CH3 | H | OCH(CH3)2 | |
| 2.031 | 2-CH3 | H | 4-Cl | H | SCH(CH3)2 | m.p. 109° |
| 2.032 | 2-Br | H | 4-Cl | H | SC(CH3)3 | |
| 2.033 | 2-Br | H | 4-Br | H | OC(CH3)3 | |
| 2.034 | 2-Br | H | 4-Br | H | NHCH(CH3)2 | |
| 2.035 | 2-Br | H | 4-Br | H | SC(CH3)3 | |
| 2.036 | 2-Br | H | 4-Br | H | S—Cyclohexyl | |
| 2.037 | 2-F | H | 4-Br | H | SC(CH3)3 | |
| 2.038 | 2-F | H | 4-Br | H | OCH(CH3)C2H5 | |
| 2.039 | 2-F | H | 4-F | H | SCH(CH3)2 | |
| 2.040 | 2-OCHF2 | H | 4-Br | H | SC(CH3)3 | |
| 2.041 | 2-OCHF2 | H | 4-Cl | H | SC(CH3)3 | |
| 2.042 | 2-CH3 | H | 4-Cl | H | SC(CH3)3 | m.p. 137–138° |
| 2.043 | 2-CH3 | H | 4-Cl | H | OC(CH3)3 | |
| 2.044 | 2-CH3 | H | 4-Cl | H | SCH2CH(CH3)2 | |
| 2.045 | 2-OCHF2 | H | 4-F | H | SCH(CH3)2 | |
| 2.046 | 2-Cl | H | 4-Br | H | SC4H9(tert.) | |
| 2.047 | 2-Cl | H | 4-Br | H | SC3H7(iso) | |
| 2.048 | 2-Cl | H | 4-Br | H | S—Benzyl | |
| 2.049 | 2-Cl | H | 4-Br | H | OC4H9(tert.) | |
| 2.050 | 2-Cl | H | 4-Cl | H | SC(CH3)2C2H5 | |
| 2.051 | 2-CH3 | H | 4-Cl | H | SC4H9(sec.) | |
| 2.052 | H | H | H | H | NHCH3 | |
| 2.053 | H | H | H | H | NHC3H7(iso) | |
| 2.054 | H | H | H | H | NHC4H9(n) | |
| 2.055 | H | H | H | H | N(CH3)2 | |
| 2.056 | H | H | H | H | OCH3 | |
| 2.057 | H | H | H | H | OC3H7(n) | |
| 2.058 | H | H | H | H | 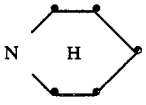 | |
| 2.059 | H | H | H | H |  | |
| 2.060 | H | H | 4-Cl | H | NHC2H5 | |
| 2.061 | H | H | 4-Cl | H | N(CH3)C2H5 | |
| 2.062 | H | H | 4-Cl | H | 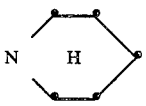 | |
| 2.063 | H | H | 4-Cl | H | 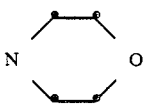 | |

TABLE 2-continued

Compounds of the formula

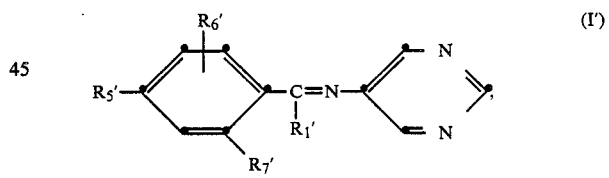

| Compound No. | R6 | R7 | R8 | R9 | R1 | Physical constants |
|---|---|---|---|---|---|---|
| 2.064 | H | H | 4-Cl | H | piperazin-1-yl (N–NH ring) | |
| 2.065 | H | H | 3-Cl | 5-Cl | $N(C_2H_5)_2$ | |
| 2.066 | 2-Cl | H | 4-Cl | H | $NHC_3H_7(n)$ | |
| 2.067 | 2-Cl | H | 4-Cl | H | piperidin-1-yl (N–H ring) | |
| 2.068 | 2-CH3 | H | 4-Cl | H | morpholin-4-yl (N–O ring) | |
| 2.069 | 2-Cl | H | 4-Cl | H | $NHC_4H_9(t)$ | m.p. 147–148° |

Analogously to the C=C double bond, the C=N double bond in the compounds of the formula I leads to different geometric isomers:

Compounds of the formula I

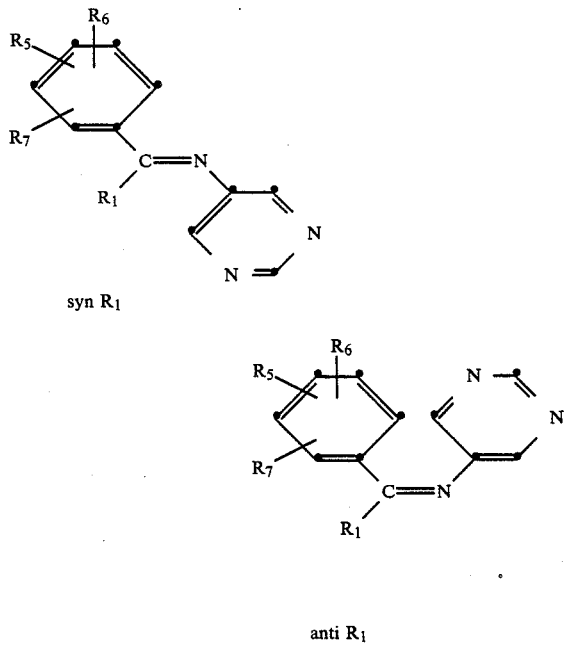

syn R1 anti R1

A mixture of the syn and anti forms is in general formed in the preparation of compounds of the formula I, the thermodynamically more favourable form preferably being formed. The substances can be used in plant protection without resolution of the isomers. Nevertheless, the use of the pure isomers may lead to a change in action.

The invention thus relates to all the isomeric compounds of the formula I in the pure form or in any desired numerical ratio to one another.

Formula I also includes compounds which are novel in comparison with those known from the prior art. The invention also relates to the novel compounds of the formula I'

$$\text{(I')}$$

in which $R_1'$ is $OR_2'$; $O-CHR_{10}'R_2'$; $N(R_3')$ $(CHR_{10}'R_4')$; $N(R_{11}')$ $(CHR_{10}'R_4')$; or $NR_3'R_4'$; $R_2'$ is ethyl; sec.-butyl; sec.-pentyl; tert.-pentyl; 2,2,3,3,3-pentafluoropropyl; 2-methoxy-1-methylethyl; (3-methyloxetan-3-yl)methyl; 2-(2-mercatptoethoxy)-ethyl; or phenyl or benzyl which is unsubstituted or mono-, di- or trisubstituted by identical or different substituents from the group comprising halogen, $C_1$–$C_4$-alkyl, $C_1$–$C_4$-alkoxy, $C_1$–$C_4$-haloalkyl, cyano and $C_1$–$C_4$-haloalkoxy; $R_3'$ is 1,1-dimethylpropyl; 3-methylbutyl; tert.-butyl; tert.-pentyl; a phenyl or benzyl radical which is unsubstituted or mono-, di-, tri- or tetrasubstituted by identical or different substituents from the group comprising halogen, $C_1$–$C_4$-alkyl, $C_1$–$C_4$-alkylcarbonyl, nitro, $C_1$–$C_4$-alkoxy, $C_1$–$C_4$-haloalkyl, $C_1$–$C_4$-alkylthio and $C_1$–$C_4$-haloalkylthio; or hydrogen; $R_4'$ is hydrogen; and $R_5'$, $R_6'$ and $R_7'$ independently of one another are hydrogen; fluorine; $C_1$–$C_4$-haloalkoxy; chlorine; bromine;

or trifluoromethyl; and $R_{10}'$ and $R_{11}'$ independently of one another are $C_1$–$C_4$-alkyl; and salts thereof with acids and bases.

The novel compounds according to formula I' can be prepared by processes analogous to the process known from European Patent A-175,651 by reacting a compound of the formula II with a compound of the formula III

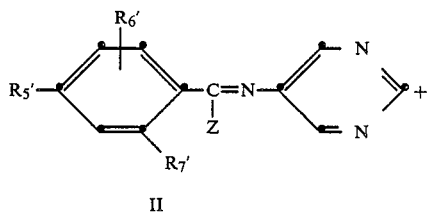

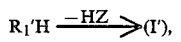

in the presence of a base, HZ being split off. Z here is a group which can be split off under the reaction conditions, such as halogen, but can also be $C_1$–$C_4$-alkylthio or phenylthio, if $R_1'H$ is $HOR_2'$, $HN(R_3')$ $(CHR_{10}'R_4')$, $HN(R_{11}')$ $(CHR_{10}'R_4')$ or $HNR_3'R_4'$, or can also be $C_1$–$C_4$-alkoxy or phenoxy if $R_1'H$ is $HNR_3'R_4'$, $HN(R_3')$ $(CHR_{10}'R_4')$ or $HN(R_{11}')(CHR_{10}'R_4')$.

The reaction of (II) with (III) to give (I') is preferably carried out with hydrogen halide being split off. Advantageous reaction temperatures are between 0° and +180° C., preferably +20° and +150° C. or at the boiling point of the solvent or solvent mixture. The use of acid-binding compositions (bases) is in general advantageous. Possible acid-binding compositions are organic and inorganic bases, for example tertiary amines, such as trialkylamines (trimethylamine, triethylamine, tripropylamine and the like), pyridines (4-dimethylaminopyridine, 4-pyrrolidylaminopyridine and the like), alcoholates, for example potassium tert.-butylate, oxides and hydroxides, carbonates and bicarbonates of alkali metals and alkaline earth metals and the salts of acetic acid, for example the alkali metal acetates.

One or more solvents or diluents which are inert in the reaction can on principle be present during the preparation of these products unless expressly specified in an individual case. Examples of suitable solvents or diluents are aliphatic and aromatic hydrocarbons, such as benzene, toluene, the xylenes and petroleum ether; halogenated hydrocarbons, such as chlorobenzene, methylene chloride, ethylene chloride, chloroform, carbon tetrachloride and tetrachloroethylene; ethers and ether-like compounds, such as dialkyl ethers (diethyl ether, diisopropyl ether, tert.-butylmethyl ether and the like), anisole, dioxane and tetrahydrofuran; nitriles, such as acetonitrile and propionitrile; N,N-dialkylated amides, such as dimethylformamide; dimethylsulfoxide; ketones, such as acetone, diethyl ketone and methyl ethyl ketone, and mixtures of such solvents with one another.

The compounds of the formula III are generally known or can be prepared by methods which are known per se.

The compounds of the formula II are known from European Patent EP-A-175,651 or can be prepared by a procedure analogous to that described therein.

The invention furthermore relates to herbicidal compositions containing a compound of the formula I' together with suitable auxiliaries and/or carriers.

As a rule, the active substances of the formula I and I' are employed successfully at application rates of 0.05 to 4 kg/ha, in particular 0.1 to 1 kg/ha. The dosage required for the desired action can be determined by experiments. It depends on the nature of the action, the development stage of the crop plant and of the weed and on the application (location, time and method), and as a result of these parameters can vary within wide limits. The compounds of the formula I can be used before or after emergence of the plants or also as feed dressing compositions.

At lower application rates, the compounds of the formula I and I' are distinguished by good selective growth inhibiting and selective herbicidal properties, which make them outstandingly suitable for use in crops of useful plants, especially in cereals, cotton, soya, maize and, in particular, rice.

The compounds of the formula I and I' also have powerful plant growth-regulating properties. The growth of both monocotyledons and dicotyledons is influenced.

In the case of many cultivated plants, an inhibition of vegetative growth permits denser planting of the crop, so that a higher yield may be obtained per soil area.

A further mechanism through which yield is increased using growth regulators is based on the fact that a greater proportion of the nutrient goes to promoting flower and fruit formation, while vegetative growth is restricted.

At higher rates of application, weeds and grasses are so severely damaged in their development that they die.

The invention also relates to herbicidal and plant growth-regulating agents which contain an active substance of the formula I or I', and to methods of combating weeds before and after emergence and for influencing the plant growth of monocotyledon and dicotyledon plants, especially grasses, tropical cover crops and side shoots.

The compounds of the formula I and I'0 are used in unmodified form or preferably as compositions together with the auxiliary agents which are usual in formulation technology and are therefore processed, in a known way, to give e.g. emulsifiable concentrates, directly sprayable or dilutable solutions, dilute emulsions, wettable powders, soluble powders, dusting agents, granulates and encapsulations in e.g. polymeric substances. Both the nature of the compositions and the application methods, such as spraying, atomizing, dusting, scattering or watering, are selected in accordance with the intended objectives and given circumstances.

The formulations, i.e. the agents, preparations or compositions containing the active substance of formula I or I' and, where appropriate, a solid or liquid additive are prepared in known ways, e.g. by intimately mixing and/or milling the active substances with extenders such as with solvents, solid carriers and, where appropriate, surface-active compounds (surfactants).

Solvents which may be used are: aromatic hydrocarbons, preferably $C_8$ to $C_{12}$ fracions, e.g. xylene mixtures or substituted naphthalenes, phthalates such as dibutyl or dioctyl phthalate, aliphatic hydrocarbons such as cyclohexane or paraffins, alcohols and glycols as well as their ethers and esters, such as ethanol, ethylene glycol, ethylene glycol monomethyl or -ethyl ether, ketones such as cyclohexanone, strongly polar solvents such as N-methyl-2-pyrrolidone, dimethyl sulfoxide or dimethylformamide, as well as nonepoxidized or epoxidized vegetable oils such as epoxidized coconut oil or soya oil; or water.

The solid carriers used, e.g. for dusting agents and dispersible powders, are, as a rule, natural rock flours such as calcite, talc, kaolin, montmorillonite or attapulgite. Highly disperse silica or highly disperse absorbent polymers can also be added to improve the physical properties. Porous types such as e.g. pumice, crushed brick, sepiolite or bentonite, and nonsorptive carrier materials e.g. calcite or sand can be used as particulate adsorptive granular carriers. In addition, a large number of pregranulated substances of an inorganic or organic nature, such as especially dolomite or comminuted plant residues, can be used.

Depending on the nature of the active substance of formula I or I' which is to be formulated nonionic, cationic and/or anionic surfactants having good emulsifying, dispersing and wetting properties come into consideration as surface-active compounds. Surfactants are also to be understood to include surfactant mixtures.

Suitable anionic surfactants can be either so-called water-soluble soaps or water-soluble synthetic surface-active compounds.

Alkali metal, alkaline-earth metal, or optionally substituted ammonium salts of higher fatty acids ($C_{10}$–$C_{22}$), such as e.g. the Na or K salts of oleic or stearic acids, or of natural mixed fatty acids which may be obtained e.g. from coconut oil or tallow oil, may be mentioned as soaps. Fatty acid methyltaurate salts may also be mentioned, furthermore.

More frequently, however, so-called synthetic surfactants are used, especially fatty sulfonates, fatty sulfates, sulfonated benzimidazole derivatives or alkylarylsulfonates.

The fatty sulfonates or sulfates are usually present in the form of alkali metal, alkalie-earth metal or optionally substituted ammonium salts and comprise an alkyl radical containing 8 to 22 C atoms, in which alkyl also includes the alkyl moiety of acyl radicals, e.g. the Na or Ca salt of ligninsulfonic acid, of dodecyl sulfate or of a fatty alcohol sulfate mixture prepared from natural fatty acids. The salts of sulfates and sulfonic acids with fatty alcohol/ethylene oxide adducts are also included among these. The sulfonated benzimidazole derivatives preferably contain 2 sulfonic acid groups and a fatty acid radical containing 8–22 C atoms. Alkylarylsulfonates are e.g. the Na, Ca or triethanolamine salts of dodecylbenzenesulfonic acid, of dibutylnaphthalenesulfonic acid or of a condensation product of naphthalenesulfonic acid with formaldehyde.

Furthermore, the corresponding phosphates, such as phosphoric acid ester salts of a p-nonylphenol-(4–14)/ethylene oxide adduct, or phospholipids may also be used.

Nonionic surfactants are principally polyglycol ether derivatives of aliphatic or cycloaliphatic alcohols, saturated or unsaturated fatty acids and alkylphenols, which can contain from 3 to 10 glycol ether groups and 8 to 20 carbon atoms in the (aliphatic) hydrocarbon radical and 6 to 18 carbon atoms in the alkyl radical of the alkylphenols.

Further suitable nonionic surfactants are water-soluble adducts of polyethylene oxide with polypropylene glycol, ethylenediaminopolypropylene glycol and alkylpolypropylene glycol with 1 to 10 carbon atoms in the alkyl chain, which contain 20 to 250 ethylene glycol ether groups and 10 to 100 propylene glycol ether group. These compounds usually contain 1 to 5 ethylene glycol units per propylene glycol unit.

As examples of nonionic surfactants there may be mentioned nonylphenolpolyethoxyethanols, castor oil polyglycol ethers, polypropylene/polyethylene oxide adducts, tributylphenoxypolyethanol, polyethylene glycol and octylphenoxypolyethoxyethanol.

Fatty acid esters of polyoxyethylenesorbitan, such as polyoxyethylenesorbitan trioleate are also suitable.

The cationic surfactants involved are principally quaternary ammonium salts whose N-substituents comprise at least one alkyl radical containing 8 to 22 C atoms and which also have lower, halogenated or unhalogenated alkyl, benzyl or lower hydroxyalkyl radicals as further substituents. The salts are preferably halides, methylsulfates or ethylsulfates, e.g. stearyltrimethylammonium chloride or benzyldi(2-chloroethyl)-ethylammonium bromide.

The surfactants customary formulaion technology are described, inter alia, in the following publications: "1985 International Mc Cutcheon's Emulsifiers and Detergents", Glen Rock, N.J., USA. Dr. Helmut Stache "Tensid Taschenbuch" Carl Hanser Verlag, Munich/Vienna 1981.

As a rule, the preparations contain 0.1 to 95%, in particular 0.1 to 80%, of active substance of formula I, 1 to 99.9% of a solid or liquid adjuvant and 0 to 25%, in particular 0.1 to 25%, of a surfactant.

Formulations which are preferred consist, in particular, of the following: (%=weight percentage)

| Emulsifiable concentrates: | |
|---|---|
| active substance of formula I or I': | 1 to 20%, preferably 5 to 10% |
| surface-active agent: | 5 to 30%, preferably 10 to 20% |
| liquid carrier: | 50 to 94%, preferably 70 to 85%. |
| Dusts: | |
| active substance of formula I or I': | 0.1 to 10%, preferably 0.1 to 1% |
| solid carrier: | 99.9 to 90%, preferably 99.9 to 99%. |
| Suspension concentrates: | |
| active substance of formula I or I': | 5 to 75%, preferably 10 to 50% |
| water: | 94 to 25%, preferably 90 to 30% |
| surface-active agent: | 1 to 40%, preferably 2 to 30%. |
| Wettable powders: | |
| active substance of formula I or I': | 0.5 to 90%, preferably 1 to 80% |
| surface-active agent: | 0.5 to 20%, preferably 1 to 15% |
| solid carrier: | 5 to 95%, preferably 15 to 90%. |
| Granulates: | |
| active substance of formula I or I': | 0.5 to 30%, preferably 3 to 15% |
| solid carrier: | 99.5 to 70%, preferably 97 to 85%. |

While concentrated compositions are preferred as commercial products, as a rule the end user uses dilute compositions. The application forms can be diluted down to 0.001% of the active substance. As a rule the rates of application are 0.005 to 5 kg a.s./ha.

The compositions can also contain further additives such as stabilizers, antifoams, viscosity regulators, binders, tackifiers, as well as fertilizers or other active substances aimed at producing specific effects.

PREPARATION EXAMPLE

H. 1a: Synthesis of 2,4-dichloro-N-(pyrimidin-5-yl)-benzimidoyl chloride 107.1 g (0.40 mol) of N-(2,4-dichlorobenzoyl)-5-aminopyrimidine are boiled under reflux with 87.2 ml (1.20 mol) of thionyl chloride in 400 ml of toluene, hydrochloric acid and sulfur dioxide being formed. The reaction has ended after 16 hours. Excess SOCl$_2$ and toluene are removed on a rotary evaporator and the residue is concentrated twice more with tetrahydrofuran for complete removal of the SOCl$_2$.

The title compound is obtained as an oil in an almost quantitative yield and can be used without further purification for the preparation of the imidoesters, thioimidoesters or amidines. For this, all of the title compound thus obtainable is dissolved in tetrahydrofuran and the solution is made up to a volume of 230 ml.

H. 1b: Synthesis of 2,4-dichloro-N'-(1,1-dimethylpropyl)-N-(pyrimidin-5-yl)-benzamidine 86.3 ml (0.15 mol) of the imide chloride solution obtainable according to preparation example 1a are diluted with 80 ml of tetrahydrofuran and the dilution is boiled under reflux with 39.5 ml (0.35 mol) of 1,1-dimethyl-propylamine for 12 hours. The amine hydrochloride which has precipitated out is filtered off with suction, the filtrate is concentrated on a rotary evaporator and the residue is chromatographed over silica gel with a mixture of 3 parts of hexane and 1 part of ethyl acetate. Removal of the solvent from the pure fractions gives 31.4 g (62.1%) of the title compound of the formula

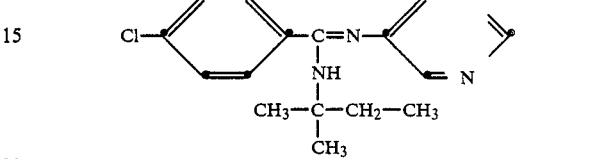

(Compound No. 1.233 in Table 1) as crystals of melting point 136°–137° C. (from ethyl acetate/cyclohexane).

The novel compounds of the formula I' mentioned below can be prepared analogously.

H1. TABLE 1

Compounds of the formula

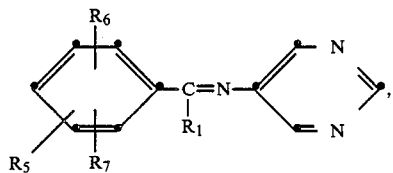

(I')

| Compound No. | R$_5$ | R$_6$ | R$_7$ | R$_1$ | Physical constants |
|---|---|---|---|---|---|
| 1.227 | 4-Cl | 2-Cl | H | O—C$_4$H$_9$ (sec) | n$_D^{22.5}$1.5655 |
| 1.228 | 4-Cl | 2-Cl | H | NH—C$_4$H$_9$ (sec) | m.p. 131–133° |
| 1.229 | 4-Cl | 2-Cl | H | OCH(CH$_3$)(C$_3$H$_7$(n)) | n$_D^{50}$1.5480 |
| 1.230 | 4-Cl | 2-Cl | H | —OCH(CH$_3$)(C$_3$H$_7$(i)) | n$_D^{50}$1.5495 |
| 1.231 | 4-Cl | 2-Cl | H | —NHCH$_2$C(CH$_3$)$_3$ | m.p. 161–162° |
| 1.232 | 4-Cl | 2-Cl | H | —NHCH$_2$CH$_2$CH(CH$_3$)$_2$ | m.p. 120–121° |
| 1.233 | 4-Cl | 2-Cl | H | —NHC(CH$_3$)$_2$C$_2$H$_5$ | m.p. 136–137° |
| 1.234 | 4-Cl | 2-Cl | H | —NHC$_2$H$_5$ | m.p. 143–144° |
| 1.235 | 4-Cl | 2-Cl | H | —NHCH$_3$ | m.p. 137–138° |
| 1.236 | 4-Cl | H | H | —NH—C(CH$_3$)$_3$ | m.p. 137–138° |
| 1.237 | 4-Cl | 2-Cl | H | —NH$_2$ | m.p. 161–162° |
| 1.238 | 4-Cl | H | H | —OC$_3$H$_7$(i) | m.p. 91–92° |
| 1.239 | 4-Cl | H | H | —NHC$_3$H$_7$(i) | m.p. 165–167° |
| 1.240 | 4-Cl | 2-Cl | H | —SCH$_2$CH$_2$Si(OC$_4$H$_9$(t))(OC$_2$H$_5$)$_2$ | Kp. 160°/0.05 mm Hg |
| 1.241 | 4-Cl | 2-Cl | H | —N(azetidinyl) | m.p. 134–135° |

H1. TABLE 1-continued

Compounds of the formula (I')

$$\text{Ar-C(R}_1\text{)=N-pyrimidine}$$

where Ar is a phenyl ring substituted with $R_5$, $R_6$, $R_7$.

| Compound No. | $R_5$ | $R_6$ | $R_7$ | $R_1$ | Physical constants |
|---|---|---|---|---|---|
| 1.242 | 4-Cl | 2-Cl | H | —NH—CH(CH$_3$)C$_3$H$_7$(i) | m.p. 146–147° |
| 1.243 | 4-Cl | 2-Cl | H | —NH-cyclobutyl | m.p. 147–148° |
| 1.244 | 4-Cl | 2-Cl | H | —OC$_2$H$_5$ | m.p. 75–76° |
| 1.245 | 4-Cl | 2-Cl | H | —O—C(CH$_3$)$_2$C≡CH | m.p. 138–139° |
| 1.246 | 4-CF$_3$ | H | H | —OC$_3$H$_7$(i) | m.p. 72–75° |
| 1.247 | 4-CF$_3$ | H | H | —O—(4-Cl-phenyl) | m.p. 81–83° |
| 1.248 | 4-Cl | 2-Cl | H | —O-phenyl | $n_D^{31}$ 1.6100 |
| 1.249 | 4-Cl | H | H | —SC$_3$H$_7$(i) | m.p. 56–57° |
| 1.250 | 4-Cl | H | H | —SC(CH$_3$)$_2$C$_2$H$_5$ | m.p. 71–73° |
| 1.251 | 4-CF$_3$ | H | H | —S—CH(C$_2$H$_5$)C$_3$H$_7$(i) | Oil |
| 1.252 | 4-Cl | 2-F | H | —O-phenyl |  |
| 1.253 | 4-Cl | 2-F | H | —O—(2-CF$_3$-phenyl) |  |
| 1.254 | 4-Cl | 2-Cl | H | —O—(4-Cl-phenyl) | m.p. 94–95° |
| 1.255 | 4-Cl | 2-Cl | H | —O—(2-Cl-phenyl) |  |

H1. TABLE 1-continued
Compounds of the formula
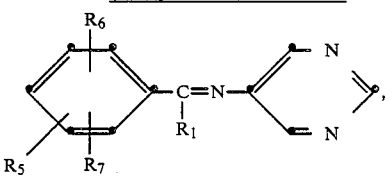
(I')
| Compound No. | R$_5$ | R$_6$ | R$_7$ | R$_1$ | Physical constants |
|---|---|---|---|---|---|
| 1.256 | 4-Cl | 2-Cl | H | 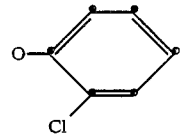 | n$_D^{25}$ 1.6145 |
| 1.257 | H | 2-F | H | O—CH(CH$_3$)$_2$ | m.p. 63–65° |
| 1.258 | H | 2-F | H | NHC(CH$_3$)$_3$ | m.p. 127–128° |
| 1.259 | H | 2-F | H | 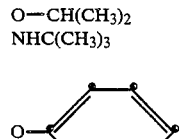 | |
| 1.260 | H | 2-F | H | 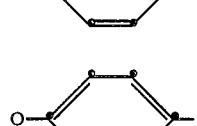 | m.p. 102–103° |
| 1.261 | H | 2-F | H |  | |
| 1.262 | H | 2-F | H | S—C(CH$_3$)$_3$ | m.p. 108–109° |
| 1.263 | 4-Cl | 2-F | H | 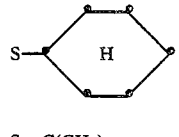 | |
| 1.264 | H | 2-Cl | H |  | |
| 1.265 | H | 2-Cl | H | 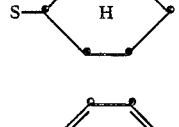 | |
| 1.266 | H | 2-F | H |  | |
| 1.267 | H | 2-Cl | H | 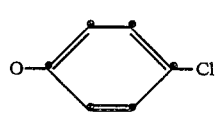 | |
| 1.268 | 4-Cl | H | H | NHC(CH$_3$)$_3$ | m.p. 137–138° |
| 1.269 | 4-Cl | 2-Cl | H | OCH$_2$CF$_2$CF$_3$ | n$_D^{31}$1.5151 |
| 1.270 | 4-Cl | 2-Cl | H | OCH(CH$_3$)CH$_2$OCH$_3$ | n$_D^{52}$1.5550 |

H1. TABLE 1-continued
Compounds of the formula
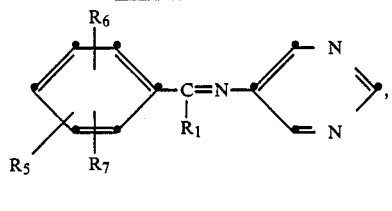 (I')
| Compound No. | R5 | R6 | R7 | R1 | Physical constants |
|---|---|---|---|---|---|
| 1.271 | 4-Cl | 2-Cl | H | 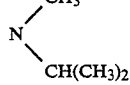 | m.p. 104–106° |
| 1.272 | 4-Cl | 2-Cl | H | SCH$_2$CH$_2$OCH$_2$CH$_2$SH | n$_D^{30}$ 1.6229 |
| 1.273 | 4-Cl | 2-Cl | H |  | m.p. 98–99° |
| 1.274 | 4-Cl | 2-Cl | H |  | m.p. 93–94° |
| 1.275 | 4-Cl | 2-Cl | H | 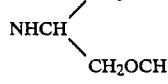 | m.p. 125–127° |
| 1.276 | 4-Cl | 2-Cl | H | 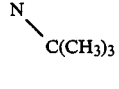 | m.p. 106–107° |
| 1.277 | 4-Cl | 2-Cl | H | NHC$_6$H$_5$ | m.p. 163–164° |
| 1.278 | 2-Cl | H | H | OCH$_2$CF$_3$ | |
| 1.279 | 2-Cl | H | H | 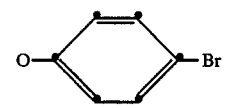 | |
| 1.280 | 2-Cl | H | H |  | m.p. 90–91° |
| 1.281 | 2-CH$_3$ | 4-CH$_3$ | H | SC(CH$_3$)$_3$ | m.p. 120–121° |
| 1.282 | 2-CH$_3$ | 4-CH$_3$ | H | NHC(CH$_3$)$_3$ | m.p. 133–135° |
| 1.283 | 2-CH$_3$ | 4-CH$_3$ | H | OC(CH$_3$)$_3$ | m.p. 60–62° |
| 1.284 | 2-CH$_3$ | 4-CH$_3$ | H | OCH$_2$CF$_3$ | |
| 1.285 | 2-CH$_3$ | 4-CH$_3$ | H | 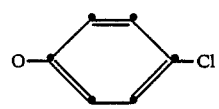 | |
| 1.286 | 4-Cl | 2-Cl | H | OCH$_2$COCH$_3$ | |
| 1.287 | 4-Cl | 2-Cl | H | 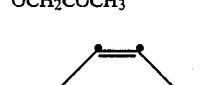 | m.p. 90–92° |

H1. TABLE 1-continued

Compounds of the formula (I')

*[Structure: phenyl ring with R5, R6, R7 substituents connected via C(R1)=N to a pyrimidine-like ring with two N atoms]*

| Compound No. | R5 | R6 | R7 | R1 | Physical constants |
|---|---|---|---|---|---|
| 1.288 | 4-Cl | 2-Cl | H | –O–C6H4–F (4-F phenoxy) | m.p. 134–135° |
| 1.289 | 4-Cl | 2-Cl | H | –O–C6H4–NO2 | m.p. 140–141° |
| 1.290 | 4-Cl | 2-Cl | H | –O–C6H4–OCH3 | m.p. 92–94° |
| 1.291 | 4-Cl | 2-Cl | H | –O–C6H4–CH3 | m.p. 94–95° |
| 1.292 | 4-Cl | 2-Cl | H | –O–C6H3(Cl)(Cl) (3,4-dichlorophenoxy) | $n_D^{50}$ 1.615 |
| 1.293 | 4-Cl | 2-Cl | H | –O–C6H4–COCH3 | m.p. 81–82° |
| 1.294 | 4-Cl | 2-Cl | H | –O–C6H4–CN | m.p. 167–168° |
| 1.295 | 4-Cl | 2-Cl | H | –O–C6H4–Cl (2-Cl phenoxy) | $n_D^{50}$ 1.612 |
| 1.296 | 4-Cl | 2-Cl | H | –NH–C6H4–Cl (2-Cl anilino) | m.p. 98–99° |
| 1.297 | 4-Cl | 2-Cl | H | –NH–C6H4–Cl (4-Cl anilino) | |

H1. TABLE 1-continued

Compounds of the formula $$\text{(I')}$$

(structure with R5, R6, R7 on benzene ring attached to C(R1)=N-pyrimidine)

| Compound No. | R5 | R6 | R7 | R1 | Physical constants |
|---|---|---|---|---|---|
| 1.298 | 4-Cl | 2-Cl | H | NH–C6H4–Br | |
| 1.299 | 4-Cl | 2-Cl | H | NH–C6H4–F | |
| 1.300 | 4-Cl | 2-Cl | H | NH–C6H4–OCH3 | m.p. 193–196° |
| 1.301 | 4-Cl | 2-Cl | H | NH–C6H4–NO2 | |
| 1.302 | 4-Cl | 2-Cl | H | NH–C6H4–CH3 | |
| 1.303 | 4-Cl | 2-Cl | H | NH–C6H3(Cl)–Cl | m.p. 160–162° |
| 1.304 | 4-Cl | 2-Cl | H | OCH2–C(CH3)(O)— (oxetane) | m.p. 110–112° |
| 1.305 | 4-Cl | 2-Cl | H | OCH(CH3)–C6H5 | m.p. 89–90° |
| 1.306 | 4-Cl | 2-Cl | H | OCH(CH(CH3)2)(C6H5) | $n_D^{50}$ 1.5769 |
| 1.307 | 4-Cl | 2-Cl | H | OCH(C(CH3)3)(C6H5) | m.p. 113–114° |

H1. TABLE 1-continued

Compounds of the formula (I')

| Compound No. | R5 | R6 | R7 | R1 | Physical constants |
|---|---|---|---|---|---|
| 1.308 | 4-Cl | 2-Cl | H | OCH(CH3)-(2-chlorophenyl) | |
| 1.309 | 4-Cl | 2-Cl | H | OCH(CH3)-(4-fluorophenyl) | |
| 1.310 | 4-Cl | 2-Cl | H | OCH(CH3)-(3-bromophenyl) | |
| 1.311 | 4-Cl | 2-Cl | H | OCH(CH3)-(3-nitrophenyl) | |
| 1.312 | 4-Cl | 2-Cl | H | OCH(C2H5)-(4-methylphenyl) | |
| 1.313 | 4-Cl | 2-Cl | H | OCH(C3H7)-(2-fluorophenyl) | |
| 1.314 | 4-Cl | 2-Cl | H | OCH(C4H9-(n))-(3-methoxyphenyl) | |

H1. TABLE 1-continued

Compounds of the formula $$\text{(I')}$$

(Structure: phenyl ring with substituents $R_5$, $R_6$, $R_7$ connected via C($R_1$)=N to a pyrimidine/diazine ring)

| Compound No. | $R_5$ | $R_6$ | $R_7$ | $R_1$ | Physical constants |
|---|---|---|---|---|---|
| 1.315 | 4-Cl | 2-Cl | H | OCH with C(CH$_3$)$_3$ and phenyl-Br substituents | |
| 1.316 | 4-Cl | 2-Cl | H | NHCH(CH$_3$)(C$_6$H$_5$) | m.p. 117–119° |
| 1.317 | 4-Cl | 2-Cl | H | NHCH(CH(CH$_3$)$_2$)(C$_6$H$_5$) | |
| 1.318 | 4-Cl | 2-Cl | H | NHCH(C$_3$H$_7$(n))(chlorophenyl) | |
| 1.319 | 4-Cl | 2-Cl | H | NHCH(CH$_3$)(methoxyphenyl) | |
| 1.320 | 4-Cl | 2-Cl | H | NHCH(C$_2$H$_5$)(nitrophenyl) | |
| 1.321 | 4-Cl | 2-Cl | H | C$_4$H$_9$(n)–N–CH(CH$_3$)(C$_6$H$_5$) | |
| 1.322 | 4-Cl | 2-F | H | OCH$_2$CF$_3$ | m.p. 66–68° |
| 1.323 | 4-Cl | 2-OCH$_2$F$_3$ | H | OCH$_2$CF$_3$ | $n_D^{50}$ 1.4931 |
| 1.324 | H | 2-F | H | OC$_4$H$_9$(t) | m.p. 73–75° |
| 1.325 | 4-Cl | H | H | NHCH(CH$_3$)$_2$ | m.p. 66–68° |
| 1.326 | 4-Cl | 2-Cl | H | NH—CH(CH$_3$)(C$_6$H$_5$) | m.p. 122–124° (+ Isomer) [α]$_D$ +63,8° ±2°(C$_2$H$_5$OH) |
| 1.327 | 4-Cl | 2-Cl | H | NH—CH(CH$_3$)(C$_6$H$_5$) | m.p. 122–124° (− Isomer) [α]$_D$ −63,6° ±2°(C$_2$H$_5$OH) |

H1. TABLE 1-continued

Compounds of the formula

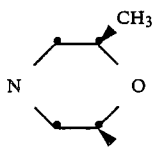

(I')

| Compound No. | $R_5$ | $R_6$ | $R_7$ | $R_1$ | Physical constants |
|---|---|---|---|---|---|
| 1.328 | 4-Cl | 2-Cl | H | OCH$_2$CBr$_3$ | m.p. 134–135° |
| 1.329 | 4-Cl | 2-Cl | H | 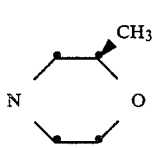 | m.p. 153–155° |
| 1.330 | 4-Cl | 2-Cl | H | 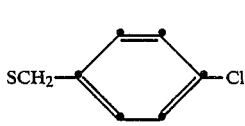 | m.p. 157–159° |
| 1.331 | 4-Cl | 2-Cl | H | NHCH(CH$_3$)CH$_2$CH(CH$_3$)$_2$ | $n_D^{50}$ 1.5490 |
| 1.322 | 4-Cl | 2-Cl | H | OCH(CH$_3$)CH$_2$N(CH$_3$)$_2$ | $n_D^{50}$ 1.5673 |
| 1.333 | 4-Cl | 2-Cl | H |  | m.p. 89–90° |
| 1.334 | H | 2-Br | H | OCH(CH$_3$)$_2$ | $n_D^{25}$ 1.5775 |
| 1.335 | H | 2-Br | H | OC(CH$_3$)$_3$ | m.p. 79–81° |
| 1.336 | H | 2-Br | H | SCH(CH$_3$)$_2$ | m.p. 84–85° |
| 1.337 | H | 2-Br | H | SC(CH$_3$)$_3$ | m.p. 119–120° |
| 1.338 | H | 2-Br | H | NHCH(CH$_3$)$_2$ | m.p. 179–181° |
| 1.339 | H | 2-Br | H | NHC(CH$_3$)$_3$ | m.p. 139–141° |
| 1.340 | H | 2-Br | H | 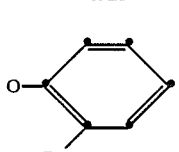 | m.p. 117–119° |
| 1.341 | H | 2-Br | H |  | m.p. 116–117° |
| 1.342 | H | 2-CH$_3$ | H | SC(CH$_3$)$_3$ | m.p. 125–127° |
| 1.343 | H | 2-CH$_3$ | H | OCH(CH$_3$)$_2$ | $n_D^{25}$ 1.5565 |
| 1.344 | H | 2-CH$_3$ | H | NHC(CH$_3$)$_3$ | |
| 1.345 | H | 2-CH$_3$ | H | SCH(CH$_3$)$_2$ | m.p. 85–86° |
| 1.346 | H | 2-CH$_3$ | H | OC(CH$_3$)$_2$ | m.p. 92–93° |
| 1.347 | H | 2-CH$_3$ | H | NHCH(CH$_3$)$_2$ | m.p. 137–138° |
| 1.348 | H | 2-CH$_3$ | H | 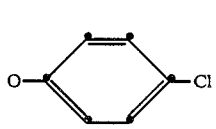 | m.p. 97–98° |
| 1.349 | 4-Cl | H | H | | |

H1. TABLE 1-continued
Compounds of the formula
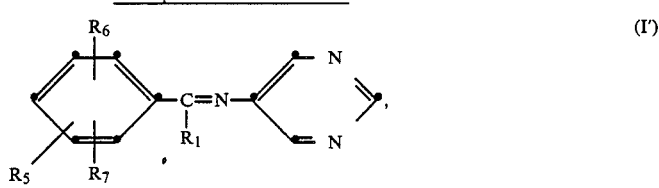
(I')
| Compound No. | R₅ | R₆ | R₇ | R₁ | Physical constants |
|---|---|---|---|---|---|
| 1.350 | 4-Cl | H | H | (2,4-dichlorophenoxy) | |
| 1.351 | 4-Cl | H | H | (2,5-dichlorophenoxy) | |
| 1.352 | 4-Cl | H | H | (2,6-dimethylphenoxy) | |
| 1.353 | 2-Cl | 4-Cl | H | (2,4-dichlorophenoxy) | |
| 1.354 | 2-Cl | 4-Cl | H | (2,4-dichlorophenoxy) | m.p. 143–145° |
| 1.355 | 2-Cl | 4-Cl | H | (2,3,4-trichlorophenoxy) | |
| 1.356 | 2-Cl | 4-Cl | H | (2,3,4-trichlorophenoxy) | m.p. 180–182° |

H1. TABLE 1-continued

Compounds of the formula (I')

[Structure: Phenyl ring with R6 (top), R5, R7 (bottom), bearing C(R1)=N– linked to a pyrimidine ring (with two N atoms)]

| Compound No. | R₅ | R₆ | R₇ | R₁ | Physical constants |
|---|---|---|---|---|---|
| 1.357 | 2-Cl | 4-Cl | H | 2-Cl,3-Cl,4-Cl-phenoxy | m.p. 144–145° |
| 1.358 | 2-Cl | 4-Cl | H | 2-Br-phenoxy | $n_D^{50}$ 1.6160 |
| 1.359 | 2-Cl | 4-Cl | H | 4-Br-phenoxy | m.p. 117–118° |
| 1.360 | 2-Cl | 4-Cl | H | 2-CH₃-phenoxy | m.p. 68–69° |
| 1.361 | 2-Cl | 4-Cl | H | 3-CH₃-phenoxy | m.p. 126–127° |
| 1.362 | 2-Cl | 4-Cl | H | 2,5-di-CH₃-phenoxy | — |
| 1.363 | 2-Cl | 4-Cl | H | 2,4-di-CH₃-phenoxy | — |
| 1.364 | 2-Cl | 4-Cl | H | 2,4-di-CH₃-phenoxy | m.p. 114–116° |

H1. TABLE 1-continued

Compounds of the formula (I')

| Compound No. | $R_5$ | $R_6$ | $R_7$ | $R_1$ | Physical constants |
|---|---|---|---|---|---|
| 1.365 | 2-Cl | 4-Cl | H | [2,6-dimethylphenoxy] | m.p. 101–102° |
| 1.366 | 2-Cl | 4-Cl | H | [4-fluorophenylthio] | m.p. 103–104° |
| 1.367 | H | 2-Cl | H | [4-fluorophenylthio] | m.p. 141–142° |
| 1.368 | H | 2-Br | H | $OCH(CH_3)C_2H_5$ | $n_D^{24}$ 1.570 |
| 1.369 | H | 2-Br | H | $SCH(CH_3)C_2H_5$ | $n_D^{24}$ 1.610 |
| 1.370 | H | 2-Br | H | [4-fluorophenoxy] | m.p. 91–92° |
| 1.371 | H | 2-Br | H | [4-fluorophenylthio] | m.p. 148–149° |

H1. TABLE 2

Compounds of the formula: (I')

| Compound No. | $R_6$ | $R_7$ | $R_8$ | $R_9$ | $R_1$ | Physical constants |
|---|---|---|---|---|---|---|
| 2.069 | 2-Cl | H | 4-Cl | H | $NHC_4H_9(t)$ | m.p. 147–148° |

Biological examples

Example B1:

Pre-emergent herbicidal action

Immediately after the test plants have been sown in seed dishes in a greenhouse, the soil surface is treated with an aqueous spray liquor corresponding to a application rate of 4 or 0.5 kg of active substance/hectare. The seed dishes are kept in a greenhouse at 22°–25° C. and 50–70% relative atmospheric humidity and the test is evaluated after 3 weeks.

In this test, the compounds of Tables 1 and 2 exhibit a potent herbicidal action.

Specifically, the herbical action shown below is found at application rates of 4 kg/ha or 0.5 kg/ha against the weeds Echinochloa crus galli and Monocharia vag. which occur preferentially in maize, rice, soya, cotton, surgarbeet and cereal crops.

The herbicidal action is evaluated according to a rating scale in which 1 is complete herbicidal action (plant has not germinated or has died)

2 to 8 are intermediate stages of decreasing action 9 is no action (as untreated control plant).

The ratings 2 to 4 can here be allocated to good herbicidal action and the ratings 6 to 8 to tolerable damage (to the crop plants).

TABLE B 1.1

| | Application rate 4 kg/ha a.s. | |
|---|---|---|
| Compound No. | ECHINOCHLOA | MONOCHARIA |
| 1.004 | 1 | 1 |
| 1.003 | 1 | 1 |
| 1.007 | 1 | 1 |
| 1.089 | 1 | 1 |

TABLE B 1.1-continued

| | Application rate 4 kg/ha a.s. | |
|---|---|---|
| Compound No. | ECHINOCHLOA | MONOCHARIA |
| 1.094 | 2 | 1 |
| 1.023 | 1 | 1 |
| 1.110 | 1 | 1 |
| 1.024 | 1 | 1 |
| 1.029 | 1 | 1 |
| 1.101 | 1 | 1 |
| 1.128 | 1 | 1 |
| 1.100 | 1 | 1 |
| 1.002 | 1 | 1 |
| 1.158 | 1 | 1 |
| 1.152 | 1 | 1 |
| 1.153 | 1 | 1 |
| 1.218 | 1 | 1 |
| 1.156 | 1 | 1 |
| 1.224 | 1 | 1 |
| 1.161 | 1 | 1 |
| 1.219 | 1 | 1 |
| 1.220 | 1 | 1 |
| 1.227 | 1 | 1 |
| 1.233 | 1 | 1 |
| 1.236 | 1 | 1 |
| 1.238 | 1 | 1 |

At an application rate of 500 g/ha a.s., the following values are found for Echinochloa crus galli, Scirpus spp., Monocharia vag. and rice plants.

TABLE B 1.2

| Compound No. | Rice | Echinochloa | Scirpus | Monocharia |
|---|---|---|---|---|
| 1.003 | 9 | 1 | 1 | 1 |
| 1.004 | 9 | 1 | 1 | 2 |
| 1.009 | 9 | 1 | 5 | 6 |
| 1.092 | 9 | 1 | 6 | 6 |
| 1.012 | 9 | 1 | 1 | 1 |
| 1.110 | 9 | 1 | 1 | 1 |
| 1.158 | 9 | 1 | 1 | 1 |
| 1.152 | 9 | 1 | 1 | 1 |
| 1.153 | 9 | 1 | 1 | 1 |
| 1.218 | 9 | 1 | 1 | 1 |
| 1.156 | 9 | 1 | 1 | 1 |
| 1.161 | 7 | 1 | 1 | 1 |
| 1.233 | 7 | 1 | 1 | 1 |
| 1.236 | 7 | 1 | 1 | 2 |

Example B2

Post-emergent herbicidal action (contact herbicide)

A number of weeds, both monocotyledons and dicotyledons, were sprayed on the plants at the post-emergence stage (in the 4- to 6-leaf stage) with an aqueous dispersion of the active substance at a dose rate of 4 kg of active substance per hectare, and the plants were kept at 24°-26° C. and 45-60% relative atmospheric humidity. 15 days after the treatment the test is assessed. The compounds of Tables 1 and 2 show a good herbicidal action in this test as well.

Example B3:

Herbicidal action towards paddy rice

The water weeds Echinochloa crus galli and Monocharia vag. are sown in plastic beakers (surface area 60 cm$^2$, volume 500 ml). After sowing, these are filled with water to soil surface leve. 3 days after sowing, the water level is increased to slightly above the soil surface (3-5 mm). The application is carried out 3 days after the sowing, by spraying the containers with the test substances. The dosage used corresponds to a quantity of active substance of 4 kg of a.s. per hectare. The plant beakers are then kept in a greenhouse under optimum growth conditions for the rice weeds, i.e. at 25°-30° C. and at high atmospheric humidity.

Assessment of the tests takes place 3 weeks after application.

The compounds of Tables 1 and 2 damage the weeds here but not the rice.

Example B4

Growth inhibition of tropical leguminous cover crops

The test plants (Centrosema plumieri and Centrosema pubescens) are cultivated until fully grown and then cut back to a height of 60 cm. After 7 days the active substance is sprayed as an aqueous emulsion. The test plants are kept at 70% relative atmospheric humidity and 6000 lux artificial light for 14 hours per day at a temperature of 27° during the day and 21° C. at night. The test is assessed 4 weeks after the application. The new growth is then evaluated in comparison with the control and is weighed and the phytotoxicity is assessed. In this test, the plants which have been treated with the active substances of Tables 1 and 2 at rates of application of up to 3000 g/ha show a marked reduction in new growth (less than 20% of the new growth of untreated control plants), but without any damage being sustained by the test plants.

Example B5

Growth regulation in soya beans

Soya beans of the "Hark" variety are sown in plastic containers in an earth/peat/sand mixture in proportions of 6:3:1, and are placed in a climatic chamber. Under optimum temperature control, illumination, fertilizer addition and watering conditions, the plants develop to the 5-6 trefoil leaf stage after approximately 5 weeks. At this point in time the plants are sprayed with an aqueous liquor of an active substance of formula I until well wetted. The concentration of active substance is to up to 100 g a.s./ha. Assessment is carried out approximately 5 weeks after the application of the active substance. In comparison with untreated control plants, the active substances of Tables 1 and 2 according to the invention effect a marked increase in the number and the weight of the husks on the leading shoot.

Example B6

Growth inhibition in cereals

The cereal varieties Hordeum vulgare (spring barley) and Secale (spring rye) are sown in plastic pots with sterilized soil in a greenhouse and are watered as required. About 21 days after sowing the seedlings are sprayed with an aqueous spray liquor of an active substance of Tables 1 and 2. The quantity of active substance is up to 100 g of active substance per hectare. 21 days after applicaton the growth of the cereal is assessed. In comparison with the untreated controls, the treated plants show a reduction in the new growth and, in some cases, an increase in the diameter of the stalks.

Example B7

Growth inhibition in grasses

The grasses Lolium perenne, Poa pratensis, Festuca ovina, Dactylis glomerata and Cynodon dactylon are sown in a greenhouse in plastic dishes with a soil/peat/sand mixture (6:3:1) and are watered as required. The emerged grasses are cut back weekly to a height of 4 cm and, about 50 days after sowing and one day after the last cutting, are sprayed with an aqueous spray liquor of an active substance of Tables 1 and 2. The amount of active substance, when converted, is up to 500 g of active substance per hectare. The growth of the grasses is assessed 21 days after application.

In comparison to the untreated control, the tested compounds of Tables 1 and 2 effect a reduction in the new growth.

Formulation examples

Example F1

Formulation examples for active substances of formula I (%=weight percentage)

| (a) Emulsifiable concentrates | (a) | (b) | (c) |
|---|---|---|---|
| Active substance according to Table 1 or 2 | 20% | 40% | 50% |
| Ca dodecylbenzenesulfonate | 5% | 8% | 5.8% |
| Castor oil polyethylene glycol ether (36 mol EO) | 5% | — | — |
| Tributylphenol polyethylene glycol ether (30 mol EO) | — | 12% | 4.2% |
| Cyclohexanone | — | 15% | 20% |
| Xylene mixture | 70% | 25% | 20% |

Emulsions of any desired concentration may be prepared from such concentrates by dilution with water.

| (b) Solutions | (a) | (b) | (c) |
|---|---|---|---|
| Active substance according to Table 1 or 2 | 80% | 10% | 5% |
| Ethylene glycol monomethyl ether | 20% | — | — |
| Polyethylene glycol MW 400 | — | 70% | — |
| N-methyl-2-pyrrolidone | — | 20% | 5% |
| Epoxidized coconut oil | — | — | 90% |

The solutions are suitable for use in the form of tiny drops.

| (c) Granules | (a) | (b) |
|---|---|---|
| Active substance according to Table 1 or 2 | 5% | 10% |
| Kaolin | 94% | — |
| Highly disperse silica | 1% | — |
| Attapulgite | — | 90% |

The active substance is dissolved in methylene chloride, the solution is sprayed onto the carrier and the solvent is then evaporated off in vacuo.

| (d) Dusts | (a) | (b) |
|---|---|---|
| Active substance according to Table 1 or 2 | 2% | 5% |
| Highly disperse silica | 1% | 5% |
| Talc | 97% | — |
| Kaolin | — | 90% |

A ready-to-use dust is obtained by mixing the carriers intimately with the active substance.

| (e) Wettable powders | (a) | (b) |
|---|---|---|
| Active substance according to Table 1 or 2 | 20% | 60% |
| Na ligninsulfonate | 5% | 5% |
| Na laurylsulfate | — | 6% |
| Octylphenol polyethylene glycol ether (7-8 mol EO) | — | 2% |
| Highly disperse silica | 5% | 27% |
| Kaolin | 70% | — |

The active substance is mixed well with the additives and the mixture is well ground in a suitable mill. Wettable powders are obtained, and these can be diluted with water to give a suspension of any desired concentration.

| (f) Extruder granules | |
|---|---|
| Active substance according to Table 1 or 2 | 10% |
| Na ligninsulfonate | 2% |
| Carboxymethylcellulose | 1% |
| Kaolin | 87% |

The active substance is mixed with the additives and the mixture is ground and moistened with water. This mixture is extruded and then dried in a stream of air.

| (g) Coated granules | |
|---|---|
| Active substance according to Table 1 or 2 | 3% |
| Polyethylene glycol (MW 200) | 3% |
| Kaolin | 94% |

The finely ground active substance is applied uniformly in a mixer to the kaolin which has been moistened with polyethylene glycol. Dust-free coated granules are obtained in this manner.

| (h) Suspension concentrate | |
|---|---|
| Active substance according to Table 1 or 2 | 40% |
| Ethylene glycol | 10% |
| Nonylphenol polyethylene glycol ether (15 mol EO) | 6% |
| Na ligninsulfonate | 10% |
| Carboxymethylcellulose | 1% |
| 37% aqueous formaldehyde solution | 0.2% |
| Silicone oil in the form of a 75% aqueous emulsion | 0.8% |
| Water | to 100% |

The active substance is mixed intimately with the additives. A suspension concentrate is obtained which can be used to prepare suspensions of any desired concentration by diluting with water.

What is claimed is:

1. A method of combating undesirable plant growth and of inhibiting plant growth, which comprises allowing a herbicidal or plant growth-inhibiting amount of a compound of the formula I

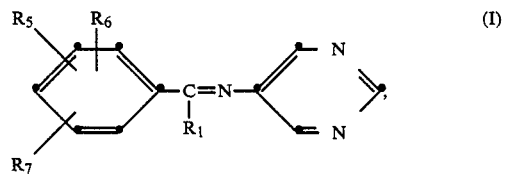

in which $R_1$ is $SR_2$; $OR_2$; $O-CHR_{10}R_2$; $N(R_3)(CHR_{10}R_4)$; $N(R_{11})(CHR_{10}R_4)$; or $NR_3R_4$; $R_2$ is $C_{10}-C_{10}$-alkyl which is unsubstituted or substituted by hydroxyl, mercapto, $C_1$–$C_4$-alkoxycarbonyl, mercaptoalkoxy, $C_1$–$C_4$-alkoxy, $C_1$–$C_4$-alkylcarbonyl, mono- or di-$C_1$–$C_4$-alkylamino, $C_1$–$C_4$-haloalkyoxy, tri-($C_1$–$C_4$-alkoxy)-silyl, cyano, nitro or phenyl; $C_1$–$C_4$-haloalkyl; $C_3$–$C_8$-alkenyl; (3-methyloxetan-3-yl)methyl; $C_3$–$C_8$-alkynyl; or a radical from the group consisting of phenyl, benzyl, $C_3$–$C_7$-cycloalkyl furanyl and furfuryl which is unsubstituted or mono-, di- or trisubstituted by identical or different substituents from the group consisting of halogen, $C_1$–$C_4$-alkyl, $C_1$–$C_4$-alkylcarbonyl, nitro, $C_1$–$C_4$-alkoxy and $C_1$–$C_4$-haloalkyl; $R_3$ and $R_4$ independently of one another are hydrogen; a phenyl or benzyl radical which is unsubstituted or mono-, di-, tri- or tetrasubstituted by identical or different substituents from the group consisting of halogen, $C_1$–$C_4$-alkyl, $C_1$–$C_4$-alkylcarbonyl, nitro, $C_1$–$C_4$-alkoxy, $C_1$–$C_4$-haloalkyl, $C_1$–$C_4$-alkylthio and $C_1$–$C_4$-haloalkylthio; $C_1$–$C_8$-alkyl; or $C_3$–$C_6$-cycloalkyl; or $R_3$ and $R_4$, together with the nitrogen atom, form a saturated 5- or 6-membered heterocyclic ring which contains up to two heteroatoms from the group consisting of N, O and S and can be mono- or disubstituted by $C_1$–$C_4$-alkyl; $R_5$ is hydrogen; halogen; $C_1$–$C_8$-alkyl; $C_1$–$C_4$-alkoxy; $C_1$–$C_4$-haloalkyl; nitro; cyano; $C_1$–$C_4$-haloalkoxy; phenylthio; di-$C_1$–$C_4$-alkylamino; phenyl; or is phenoxy which is unsubstituted or substituted by the radicals $R_8$ and $R_9$; and $R_6$, $R_7$, $R_8$ and $R_9$ independently of one another are hydrogen; halogen; $C_1$–$C_8$-alkyl; $C_1$–$C_4$-haloalkyl; $C_1$–$C_4$-alkoxy; $C_1$–$C_4$-haloalkoxy; nitro; cyano; or di-$C_1$–$C_4$-alkylamino; and $R_{10}$ and $R_{11}$ independently of one aother are $C_1$–$C_4$-alkyl; or a salt of a compound of the formula I with an acid or base, to act on the plants or on the environment of the plants.

2. The method according to claim 1, wherein a compound of the formula I in which $R_1$ is $SR_2$; $OR_2$; O—$CHR_{10}R_2$; $N(R_3)(CHR_{10}R_4)$; $N(R_{11})(CHR_{10}R_4)$ or $NR_3R_4$; $R_2$ is $C_1$–$C_6$-alkyl which is unsubstituted or substituted by hydroxyl, mercapto, methoxycarbonyl, phenyl, di-$C_1$–$C_2$-alkylamino, cyano, nitro, $C_1$–$C_2$-alkoxy, acetyl or tri-($C_1$–$C_4$-alkoxy)silyl; $C_7$–$C_{10}$-alkyl; (3-methyl-oxetan-3-yl)methyl; $C_1$–$C_3$-fluoroalkyl; propenyl; $C_3$–$C_5$-alkynyl; furanyl; furfuryl; or phenyl which is unsubstituted or substituted by fluorine, chlorine, methyl, methoxy or trifluoromethyl; or $C_5$–$C_6$-cycloalkyl which is unsubstituted or monosubstituted by chlorine; $R_3$ is hydrogen; or $C_1$–$C_3$-alkyl; $R_4$ is hydrogen; $C_1$–$C_5$-alkyl; a phenyl radical which is unsubstituted or mono- or disubstituted by methyl, methoxy, fluorine, chlorine, bromine or nitro; or $C_3$–$C_6$-cycloalkyl; or $R_3$ and $R_4$, together with the nitrogen atom, are piperazinyl; pyrrolidinyl; or morpholinyl or piperidinyl which is unsubstituted or mono- or disubstituted by methyl or ethyl; $R_5$ is bonded in the para-position relative to the carbimino grup and is hydrogen; fluorine; chlorine; bromine; $C_1$–$C_4$-alkyl; dimethylamino; trifluoromethyl; phenylthio; nitro; iodine; cyano; methoxy; phenyl; or is phenoxy which is unsubstituted or substituted by the radical $R_8$ and $R_9$; and $R_6$ and $R_7$ independently of one another are hydrogen; chlorine; fluorine; bromine; iodine; methyl; trifluoromethyl; 2,2,2-trifluoroethoxy; nitro; difluoromethyl; or dimethylamino; and $R_8$ and $R_9$ independently of one another are hydrogen; fluorine; chlorine; bromine; methyl; or trifluoromethoxy; and $R_{10}$ and $R_{11}$ independently of one another are $C_1$–$C_4$-alkyl; or a salt of a compound of the formula I with an acid or base, is allowed to act as a herbicide or growth regulator on plants or their environment.

3. The method according to claim 1, wherein a compound of the formula I in which $R_1$ is $SR_2$; $OR_2$; O—$CHR_{10}R_2$; $N(R_3)(CHR_{10}R_4)$; $N(R_{11})(CHR_{10}R_4)$ or $NR_3R_4$; $R_2$ is $C_1$–$C_6$-alkyl; 2-[tri-(ethoxy)-silyl]ethyl; 2-[tri-(methoxy)-silyl]ethyl, 2-[(diethoxy)-(tert.-butoxy)-silyl]ethyl; propenyl; $C_3$–$C_5$-alkynyl; cyclohexyl; 4-chlorophenyl; p-tolyl; m-tolyl; benzyl; 4-chlorobenzyl; furfuryl; 2,2,3,3,3-pentafluoropropyl; 2-chlorophenyl; 2-bromophenyl; 3-bromophenyl; 3,5-dichlorophenyl; 2,3,5-trichlorophenyl; 4-fluorophenyl; 3,4-dimethylphenyl; 3,5-dimethylphenyl; 2-dimethylamino-2-methylethyl; 2-methoxy-1-methylethyl or 2,2,2-trifluoroethyl; $R_3$ is hydrogen; methyl; or ethyl; $R_4$ is hydrogen; $C_2$–$C_5$-alkyl; phenyl; cyclopropyl or cyclohexyl; or $R_3$ and $R_4$, together with the nitrogen atom, are 2,6-dimethylmorpholinyl or 3-ethylpiperidinyl; $R_5$ is bonded in the para-position relative to the carbimino group and is hydrogen; fluorine; chlorine; bromine; iodine; methyl; trifluoromethyl; nitro; tert.-butyl; or methoxy; $R_6$ is hydrogen; chlorine; fluorine; 2,2,2-trifluoroethoxy or iodine; and $R_7$ is hydrogen; $R_8$ is hydrogen; or chlorine; and $R_9$ is hydrogen; and $R_{10}$ and $R_{11}$ independently of one another are $C_1$–$C_4$-alkyl; is allowed to act as a herbicide or growth regulator on plants or their environment.

4. The method according to claim 1, wherein a compound of the formula I in which $R_1$ is $SR_2$; $OR_2$; or $NR_3R_4$; $R_2$ is $C_1$–$C_6$-alkyl; phenyl; chlorophenyl; or tolyl; $R_3$ is hydrogen; and $R_4$ is $C_1$–$C_5$-alkyl; and $R_5$ is in the para-position relative to the carbimino group and is hydrogen; fluorine; chlorine; or bromine; and $R_6$ is hydrogen; fluorine; chlorine; or bromine; and $R_7$ is hydrogen; is allowed to act as a herbicide or growth regulator on plants or their environment.

5. The method according to claim 1, wherein a compound of the formula I in which $R_1$ is $SR_2$ is allowed to act on plants or their environment.

6. The method according to claim 1, wherein a compound of the formula I in which $R_1$ is $OR_2$ or $OCHR_{10}R_2$ is allowed to act on plants or their environment.

7. The method according to claim 1, wherein a compound of the formula I in which $R_1$ is $NR_3R_4$, $N(R_3)(CHR_{10}R_4)$ or $N(R_{11})(CHR_{10}R_4)$ is allowed to act on plants or their environment.

8. The method according to claim 1 for combating undesirable plant growth in rice.

* * * * *